US012611466B2

(12) United States Patent
Zhang et al.

(10) Patent No.: US 12,611,466 B2
(45) Date of Patent: Apr. 28, 2026

(54) MODIFIED VECTOR, CONSTRUCTION METHOD, AND APPLICATION OF MODIFIED AAV-8 SEROTYPE FOR GENE TARGETING AND EXPRESSION

(71) Applicant: SHANGHAI OPHTHAL-BRIGHT BIOMEDICINE TECHNOLOGY, Shanghai (CN)

(72) Inventors: Shiqing Zhang, Shanghai (CN); Xiaojiang Wu, Shanghai (CN); Liping Gu, Shanghai (CN); Hong Yu, Shanghai (CN)

(73) Assignee: SHANGHAI OPHTHAL-BRIGHT BIOMEDICINE TECHNOLOGY, Shanghai (CN)

( * ) Notice: Subject to any disclaimer, the term of this patent is extended or adjusted under 35 U.S.C. 154(b) by 0 days.

(21) Appl. No.: 18/849,551

(22) PCT Filed: Aug. 29, 2022

(86) PCT No.: PCT/CN2022/115529
§ 371 (c)(1),
(2) Date: Sep. 23, 2024

(87) PCT Pub. No.: WO2024/044892
PCT Pub. Date: Mar. 7, 2024

(65) Prior Publication Data
US 2025/0108127 A1     Apr. 3, 2025

(51) Int. Cl.
*A61K 48/00*     (2006.01)
*C12N 7/00*      (2006.01)
*C12N 15/86*     (2006.01)

(52) U.S. Cl.
CPC ........... *A61K 48/0041* (2013.01); *C12N 7/00* (2013.01); *C12N 15/86* (2013.01); *C12N 2750/14122* (2013.01); *C12N 2750/14143* (2013.01); *C12N 2750/14152* (2013.01)

(58) Field of Classification Search
CPC ....... C12N 7/00; C12N 15/86; A61K 48/0041
See application file for complete search history.

(56) References Cited

U.S. PATENT DOCUMENTS

| 7,282,199 | B2 * | 10/2007 | Guangping et al. |
| 9,585,971 | B2 | 3/2017 | Deverman et al. |
| 2015/0376240 | A1 | 12/2015 | Cronin et al. |
| 2021/0363192 | A1 | 11/2021 | Anguela et al. |
| 2024/0352096 | A1 * | 10/2024 | Wu |

FOREIGN PATENT DOCUMENTS

| CN | 109661470 A | 4/2019 |
| CN | 115044614 A | 9/2022 |

OTHER PUBLICATIONS

Pupo A, Fernández A, Low SH, François A, Suárez-Amaran L, Samulski Rj. AAV vectors: The Rubik's cube of human gene therapy. Mol Ther. 2022;30(12):3515-3541. doi: 10.1016/j.ymthe. 2022.09.015 (Year: 2022).*
Mohammadsharif Tabebordbar, et al., Directed evolution of a family of AAV capsid variants enabling potent muscle-directed gene delivery across species, Cell., 2021, pp. 4919-4938, vol. 184 No. 19.
Lian Wenchang, et al., Modify AAV Capsid Protein Via Genetic Engineering, Biotechnology Bulletin, 2011, pp. 22-26,32, vol. 12.

* cited by examiner

*Primary Examiner* — Maria G Leavitt
*Assistant Examiner* — Kodye Lee Abbott
(74) *Attorney, Agent, or Firm* — Bayramoglu Law Offices LLC

(57)          ABSTRACT

A modified vector of adenovirus-associated virus serotype 8 (AAV-8) for gene targeting and expression is provided, wherein the modified vector includes serotype coat amino acid sequence, insertion site and insertion amino acid sequence. A 10-amino acid sequence set forth in SEQ ID NO.3 is inserted between amino acids at positions 590 and 591 that are set forth in SEQ ID NO.2 of the AAV-8 serotype coat protein: LARGDSTKSA, wherein amino acids at positions 1, 2 and 10 are protective amino acids, and amino acids at positions 3 to 9 are screened amino acid sequences. In addition, the present invention also discloses construction method and application of the modified vector are also provided.

2 Claims, 20 Drawing Sheets
(18 of 20 Drawing Sheet(s) Filed in Color)

Specification includes a Sequence Listing.

MODIFIED VECTOR, CONSTRUCTION METHOD, AND APPLICATION OF MODIFIED AAV-8 SEROTYPE FOR GENE TARGETING AND EXPRESSION

CROSS REFERENCE TO THE RELATED APPLICATIONS

This application is the national phase entry of International Application No. PCT/CN2022/115529, filed on Aug. 29, 2022, the entire contents of which are incorporated herein by reference.

SEQUENCE LISTING

The instant application contains a Sequence Listing which has been submitted in XML format via EFS-Web and is hereby incorporated by reference in its entirety. Said XML copy is named GBSHHY029_Sequence_Listing.xml, created on Sep. 12, 2024, and is 22,173 bytes in size.

TECHNICAL FIELD

The present invention belongs to the field of genetic engineering and biotechnology, more specifically relates to a sreening, construction, and application of a modified AAV-8 serotype for gene targeting and expression.

BACKGROUND

AAV is a DNA-defective, non-pathogenic parvovirus. Recombinant adeno-associated virus vectors (rAAV) are derived from non-pathogenic, wild-type adeno-associated viruses with low immunogenicity, good safety, a wide host range, high infection efficiency, and strong tissue specificity, which are ideal gene expression vector, and have been approved by FDA for use in clinical trials.

Currently, AAV viral coat proteins are used in AAV virus packaging systems, more commonly used are traditional wild-type AAV capsid proteins of AAV1, 2, 5, 8, and 9, which have specificity of different tissues or cells. Although these natural, wild-type AAV virus capsids can effectively target AAV to specific tissues for exogenous gene expression, such as, AAV1 can efficiently infect skeletal muscle cells, AAV2 can target retinal cells, AAV8 can efficiently deliver exogenous genes to liver cells, and AAV9 has the ability to cross the blood-brain barrier and express exogenous gene in central nervous system and brain, etc. The natural tropism of virus determines the basis of targeted delivery therapy, on the other hand, and also provides a platform for us to modify these viral capsids with higher permeation capacity, longer expression time and lower immunogenicity.

Given that AAV has been widely used in preclinical research of a variety of diseases, It is important to modify and optimize the targeting of natural, wild-type AAV coat protein. Currently, there are many methods for modifying and optimizing AAV capsid proteins, including DNA shuffling technology, site-directed mutagenesis of capsid protein amino acids, and artificial insertion or deletion of amino acid sequences to modify capsid protein, etc. In these methods described herein, based on phage display-display system techniques developed in recent years, it is an efficient and feasible screening method to screen specific targeting short peptide from random peptide library and insert said specific targeting short peptide into the specific site of wild-type AAV coat protein.

The therapy of ophthalmic diseases mediated by AAV holds great prospect in clinical applications, having advantages in the clear structure of the eyeball tissue and the transparent refractive stroma, which is easy to observe, locate and manipulate. Additionally, ocular tissues possess immunological tolerance, that is, it is not easy to reject foreign substances, such as adenovirus (AdV), adeno-associated virus (AAV), etc., which has great potential of the feasibility of the therapy of ophthalmic diseases whether single or multiple genes. Epidemiological data indicate that most people around the world have been infected with wild-type AAV, and AAV2 antibody has been already present in newborn infants, so AAV2 is more likely to cause autoimmunity and acquired immune responses in the human body. AAV8, originally isolated from rhesus monkeys, which is more unique in serology, has minimal cross-reactivity with other serotypes, and is much less immunogenic than AAV. In many ophthalmic diseases, the retina of patients is often fragile. Therefore, infections are typically conducted via intravitreal infusion rather than subretinal infusion in clinical practice. Relevant experiments have shown that said wild-type AAV8 has relatively low efficiency in translocating from the vitreous to the posterior segments of the eye, such as the retina, via intravitreal infusion, and this has been observed in the clinical application of ophthalmic diseases. Hence, we propose to use a directed evolution method to insert a 10-amino acid sequence, wherein said 10-amino acid sequence comprising 7 random amino acid segments and 3 protective amino acids, between the amino acids at positions 590 and 591 of the AAV-8 wild-type capsid, insert the random short peptide display library. By in vitro expression method, a new AAV modified capsid with good penetration, strong infectivity and low immunogenicity was quickly and effectively screened from a random short peptide library in target tissues.

SUMMARY

One of the technical problems to be solved by the present invention is to screen a modified vector of AAV-8 serotype for gene targeting and expression.

The second technical problem to be solved by the present invention is to provide a construction method of said modified vector. In this present invention, a novel AAV-8 modified capsid, designated AAV8-590RGD, capable of infecting both the retina and retinal pigment epithelial cells, is screened by eyeball intravitreal infusion By in vitro evolutionary screening method, 10 amino acids are inserted between the amino acids at positions 590 and 591 of the AAV-8 wild-type capsid, wherein said 10 amino acids comprising 7 random amino acids, 2 protective amino acids LA at the 5'end and 1 protective amino acid A at the 3' end. After two rounds of virus packaging, each AAV virus capsid carries a unique and distinct 10-amino acid sequence insertion, corresponding to its AAV genome sequence. These viruses are then injected into the vitreous body of mice. About one week later, the retina and choroid of said mice are collected, the genome is extracted and analyzed. To observe whether AAV virus penetrate from the vitreous body to the retina and the retinal pigment epithelial layer.

The third technical problem to be solved by the present invention is to provide the application of the modified vector AAV8-590RGD.

To solve the technical problems mentioned above, the present invention adopts the following technical solutions:

In the first aspect, the present invention provides a modified vector of AAV-8 serotype for gene targeting and expression, wherein a 10-amino acid sequence set forth in SEQ ID NO: 3 is inserted between amino acids at positions 590 and 591 that are set forth in SEQ ID NO: 2 of said AAV-8 serotype coat protein: LARGDSTKSA, wherein amino acids at positions 1, 2 and 10 are protective amino acids, and amino acids at positions 3 to 9 are screened amino acid sequences.

Said 10-amino acid sequence set forth in SEQ ID NO: 3, wherein its corresponding base sequence is set forth in SEQ ID NO: 4.

The nucleotide sequence of said modified vector of AAV-8 serotype for gene targeting and expression is set forth in SEQ ID NO: 1.

Said amino acid sequence LARGDSTKSA inserted in said modified vector is used in the outer capsid for AAV virus packaging, or used in the linkage and targeting of biological macromolecules, antibody drugs, peptides, and chemical small molecules.

The present invention provides that constructing AAV vector comprising a 30-base sequence corresponding to a 10-amino acid sequence (7 random amino acids and 3 protective amino acids) set forth in SEQ ID NO: 3, comprising CAP gene, REP gene, and Ampicillin resistance gene selectively labeled. The corresponding 30-base sequence set forth in SEQ ID NO: 4 is inserted between the corresponding base sequence of amino acids at positions 590 and 591 of said CAP gene. Ampicillin resistance gene is antibiotic resistance gene, which aims to make bacteria that have been successfully vector-introduced resistant to antibiotics, then screen and amplify said AAV vector.

In the second aspect, the present invention also provides a construction method of said modified vector, comprising the following steps:

Step 1: synthesizing a stochastic 21-base sequence, adding protective bases TTGGCT at the 5'-end, adding protective bases GCC at the 3'-end, and inserting said sequence into said corresponding base sequence of said amino acids at positions 590 and 591 of the AAV-8 Cap gene, forming the AAV capsid vector;

Step 2: transforming said AAV capsid vector into several electrocompetent cells, each electrocompetent cell cultivated over night in LB medium. The next day, taking bacterial solution from each medium, mixing said bacterial solution, inoculating said bacterial solution into LB medium, and shaking overnight, the remaining bacterial solution stored in glycerol. Performing plasmid extraction to obtain a mixed vector library, wherein said mixed vector library is designated pAAV8-590-7aa;

Step 3: packaging and purifying AAV virus by using pAAV8-590-7aa and AAV-8 Cap plasmids together with adjuvant plasmids, said virus designated AAV library transfer shuttles. Performing a second round of AAV virus packaging and purification with said AAV library transfer shuttles co-infected with adenovirus into Hek293T cells;

Step 4: administering said AAV virus of the second round to C57BL/6J strain mice via eye drops, collecting retina and choroid layers, extracting genomic DNA from said retina and choroid layers, detecting and sequencing the 21 amino acids following the base sequence corresponding to the amino acid at position 590 of AAV-8 Cap gene;

Step 5: analyzing the sequencing results, amplifying random sequence using PCR, and repeating Step 1 for the second round of screening. Analyzing the sequencing results again to determine the 10 amino acids sequence, inserting said 10 amino acids sequence into the positions 590 and 591 of the AAV-8 Cap gene, packaging AAV virus, infecting the retina by intravitreal infusion, infecting the hippocampus by stereotactic infusion, conducting cell infection experiments in vitro cell, comparing the infection differences between AAV-8 and AAV8-590RGD;

As a preferable technical solution of the present invention, in Step 3, said AAV library transfer shuttles co-infected with adenovirus into Hek293T cells, specifically that said AAV library transfer shuttles co-infected with adenovirus into Hek293T cells at a multiplicity of infection of 1.

In the third aspect, the present invention provides an application of said vector. An application of said vector in the preparation of product for infecting the retina, wherein the infection of the retina can be achieved by eye drops or intravitreal infusion, but is not limited to said two dosing methods. An application of said vector in the preparation of product for infecting the cerebellum, hippocampus, motor cortex, or striatum by stereotactic infusion, wherein the infection of the cerebellum, hippocampus, motor cortex, or striatum by stereotactic infusion. An application of said vector in the infection of retinal ganglion cell, Neuro2A cell, U251 cell, ARPE-19 cell, SH-SY-5Y cell, BV2 cell, primary HBMEC isolated cell, JURKAT cell, K562 cell, and THP1 cell in vitro. The application and comparison of serotypes and wild-type AAV-8 in infecting different tissues and cells.

The above terms are defined below.

AAV capsid vector: capable of expressing adeno-associated virus protein capsid, also known as the capsid. The capsid is an oligomer formed by the viral capsid protein subunits. The function of the capsid is to encapsulate the genetic material of the virus.

AAV-8 type: a type of AAV, originally isolated from rhesus monkeys, originally isolated from rhesus monkeys, which is more unique in serology, has minimal cross-reactivity with other serotypes, and is much less immunogenic than AAV2.

AAV-8 serotype capsid protein: the protein coat of the AAV-8 virus, which encapsulates the genetic material of AAV-8.

Wild-type AAV-8 serotype: antigen of AAV-8 virus that is natural, unmodified, or unengineered.

Gene targeting and expression: delivering the target gene specifically to the target cells or tissues and enabling gene expression.

Protective amino acid: the amino acid that connects the inserted amino acid with the original capsid amino acid. It is used to stabilize the protein conformation and function.

Random amino acid sequence: a random base sequence synthesized from random base sequences corresponding to the corresponding random amino acid sequence.

Compared with the prior art, the present invention has the following beneficial effects: the modified vector of the present invention includes serotype coat amino acid sequence, insertion site and insertion amino acid sequence. On the basis of the AAV-8 wild-type serotype, a 10-amino acid sequence, wherein said 10-amino acid sequence comprising 7 random amino acid segments and 3 protective amino acids, is inserted between the amino acids at positions 590 and 591 of the AAV-8 wild-type capsid, the random short peptide display library is inserted. By in vitro expression method, a new AAV modified capsid with good penetration, strong infectivity and low immunogenicity was quickly and effectively screened from a random short peptide library in target tissues. The modified vector of the present invention has stronger fluorescence, can be observed obviously and intuitively. Exogenous gene can be efficiently expressed in the targeted tissues in vivo. Under the condition of using the same viral load, it has better expression effect than the wild type serotype in the present invention. Furthermore, it has less liver leakage expression than the wild type serotype by eyeball intravitreal infusion in the present invention.

Compared to the wild-type AAV-8 serotype, the application and comparison experiments of the modified vector AAV8-590RGD serotype in infecting different tissues and cells show that the present invention has the following beneficial effects:

AAV-8 modified serotypes were better able to infect the mice retina (FIGS. 3A-3B) (FIGS. 4A-4B) by intravitreal infusion and have less liver leakage expression (FIGS. 5A-5B).

AAV-8 modified serotypes were better able to infect in vitro, including but not limited to retinal ganglion cell (FIGS. 6A-6B), Neuro2A cell (FIGS. 7A-7B), U251 cell (FIGS. 8A-8B), SH-SY-5Y cell (FIGS. 10A-10B), primary HBMEC cell (FIGS. 12A-12B), and JURKAT cell (FIGS. 13A-13B).

AAV-8 modified serotypes were better able to infect via stereotactic injection, including but not limited to the mouse cerebellum (FIGS. 16A-16B), hippocampus (FIGS. 17A-17B), and striatum (FIGS. 19A-19B).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 3A-3B show images of AAV8-590RGD serotype packaged virus, and wild AAV8 serotype packaged virus, separately injected by intravitreal infusion and infected the retina (plating) screened in Embodiment 5 of the present invention, wherein FIG. 3A represents wild AAV8 serotype packaged virus, FIG. 3B represents AAV8-590RGD serotype packaged virus screened in the present invention.

FIGS. 4A-4B show images of AAV8-590RGD serotype packaged virus, and wild AAV8 serotype packaged virus, separately injected by intravitreal infusion and infected the retina (sections) screened in Embodiment 5 of the present invention, wherein FIG. 4A represents wild AAV8 serotype packaged virus, FIG. 4B represents AAV8-590RGD serotype packaged virus screened in the present invention.

FIGS. 5A-5B show images of AAV8-590RGD serotype packaged virus, and wild AAV8 serotype packaged virus, separately injected by intravitreal infusion and infected the eyeball, brain, and various organs in vivo live imaging screened in Embodiment 5 of the present invention, wherein FIG. 5A represents wild AAV8 serotype packaged virus, FIG. 5B represents AAV8-590RGD serotype packaged virus screened in the present invention.

FIGS. 6A-6B show images of AAV8-590RGD serotype packaged virus, and wild AAV8 serotype packaged virus, infected the retinal ganglion cell screened in Embodiment 4 of the present invention, wherein FIG. 6A represents wild AAV8 serotype packaged virus, FIG. 6B represents AAV8-590RGD serotype packaged virus screened in the present invention.

FIGS. 7A-7B show images of AAV8-590RGD serotype packaged virus, and wild AAV8 serotype packaged virus, infected Neuro2A cell screened in Embodiment 4 of the present invention, wherein FIG. 7A represents wild AAV8 serotype packaged virus, FIG. 7B represents AAV8-590RGD serotype packaged virus screened in the present invention.

FIGS. 8A-8B shows images of AAV8-590RGD serotype packaged virus, and wild AAV8 serotype packaged virus, infected U251 cell screened in Embodiment 4 of the present invention, wherein FIG. 8A represents wild AAV8 serotype packaged virus, FIG. 8B represents AAV8-590RGD serotype packaged virus screened in the present invention.

FIGS. 9A-9B show images of AAV8-590RGD serotype packaged virus, and wild AAV8 serotype packaged virus, infected ARPE-19 cell screened in Embodiment 4 of the present invention, wherein FIG. 9A represents wild AAV8 serotype packaged virus, FIG. 9B represents AAV8-590RGD serotype packaged virus screened in the present invention.

FIGS. 10A-10B show images of AAV8-590RGD serotype packaged virus, and wild AAV8 serotype packaged virus, infected SH-SY-5 cell screened in Embodiment 4 of the present invention, wherein FIG. 10A represents wild AAV8 serotype packaged virus, FIG. 10B represents AAV8-590RGD serotype packaged virus screened in the present invention.

FIGS. 11A-11B show images of AAV8-590RGD serotype packaged virus, and wild AAV8 serotype packaged virus, infected AAV8-590RGD cell screened in Embodiment 4 of the present invention, wherein FIG. 11A represents wild AAV8 serotype packaged virus, FIG. 11B represents AAV8-590RGD serotype packaged virus screened in the present invention.

FIGS. 12A-12B show images of AAV8-590RGD serotype packaged virus, and wild AAV8 serotype packaged virus, infected primary isolated HBMEC cell screened in Embodiment 4 of the present invention, wherein FIG. 12A represents wild AAV8 serotype packaged virus, FIG. 12B represents AAV8-590RGD serotype packaged virus screened in the present invention.

FIGS. 13A-13B show images of AAV8-590RGD serotype packaged virus, and wild AAV8 serotype packaged virus, infected JURKAT cell screened in Embodiment 4 of the present invention, wherein FIG. 13A represents wild AAV8 serotype packaged virus, FIG. 13B represents AAV8-590RGD serotype packaged virus screened in the present invention.

FIGS. 14A-14B show images of AAV8-590RGD serotype packaged virus, and wild AAV8 serotype packaged virus, infected K562 cell screened in Embodiment 4 of the present invention, wherein FIG. 14A represents wild AAV8 serotype packaged virus, FIG. 14B represents AAV8-590RGD serotype packaged virus screened in the present invention.

FIGS. 15A-15B show images of AAV8-590RGD serotype packaged virus, and wild AAV8 serotype packaged virus, infected THP1 cell screened in Embodiment 4 of the present invention, wherein FIG. 15A represents wild AAV8 serotype packaged virus, FIG. 15B represents AAV8-590RGD serotype packaged virus screened in the present invention.

FIGS. 16A-16B show images of AAV8-590RGD serotype packaged virus, and wild AAV8 serotype packaged virus, infected the mice cerebellum screened in Embodiment 5 of the present invention, wherein FIG. 16A represents wild AAV8 serotype packaged virus, FIG. 16B represents AAV8-590RGD serotype packaged virus screened in the present invention.

FIGS. 17A-17B show images of AAV8-590RGD serotype packaged virus, and wild AAV8 serotype packaged virus, infected the mice hippocampus screened in Embodiment 5 of the present invention, wherein FIG. 17A represents wild AAV8 serotype packaged virus, FIG. 17B represents AAV8-590RGD serotype packaged virus screened in the present invention.

FIGS. 18A-18B show images of AAV8-590RGD serotype packaged virus, and wild AAV8 serotype packaged virus, infected the mice motor cortex screened in Embodiment 5 of the present invention, wherein FIG. 18A represents wild AAV8 serotype packaged virus, FIG. 18B represents AAV8-590RGD serotype packaged virus screened in the present invention.

FIGS. 19A-19B show images of AAV8-590RGD serotype packaged virus, and wild AAV8 serotype packaged virus, infected the mice striatum screened in Embodiment 5 of the present invention, wherein FIG. 19A represents wild AAV8 serotype packaged virus, FIG. 19B represents AAV8-590RGD serotype packaged virus screened in the present invention.

DETAILED DESCRIPTION OF THE EMBODIMENTS

The present invention will be further exemplified below with reference to specific embodiments. However, it should be understood that the specific embodiments described herein are presented by way of example and are not intended to limit the scope of the invention. The key features of the present invention can be applied to various embodiments within the scope of the invention without departing from its principles.

Embodiment 1: Vector Construction

The specific method and step for sequence design and synthesis is as follows:

(1) Design the BsmBI-AAV8 Cap (482-655aa)-BsmBI gene DNA fragment based on the gene information of AAV8 Cap packaging plasmid in GeneBank. Synthesize the double-stranded DNA molecule.

(2) Obtain PCR products by using the synthesized primers: pAAV8-590-7aa-F (set forth in SEQ ID NO: 5, the forward primer, also known as Primer1) and pAAV8-590-7aa-R (set forth in SEQ ID NO: 6, the reverse primer, also known as Primer2) to perform PCR on the double-stranded DNA molecule synthesized in step (1).

Wherein in step (2), said PCR system is as follows: 32.5 μL H2O, 10 μL 5× Buffer (containing Mg2+), 4 μL dNTPs (each 2.5 mM), 1 μL forward primer Primer1 (+), 1 μL reverse primer Primer2 (−) (10 μM), 1 μL target gene template DNA, and 0.5 μL PrimeSTAR enzyme, making up the reaction system.

Wherein said PCR program is as follows: 98° C., denaturation for 3 minutes; annealing at 98° C. for 10 seconds, 55° C. for 15 seconds, 72° C. for 1 minute, repeating for 30 cycles; extension at 72° C. for 10 minutes.

The specific method and step for inserting the sequence into the Ssite is as follows:

1) Use the restriction endonuclease BsmBI to digest the virus vector Rep-AAV8-Cap, and recover the vector backbone.

2) Recombine the PCR product from step (2) with the vector backbone from step (1), transform it into *Escherichia coli*, select positive colonies and extract plasmids of said positive colonies to obtain the recombinant vector.

Wherein in step 1), said enzyme digestion system is as follows: BsmBI: 1 μL, buffer: 3 μL, Rep-AAV8-Cap plasmid: 1 μg, supplemented with water to 30 μL; digest at 37° C. for 4 hours.

Wherein in step 2), said recombination system is as follows: recombination enzyme: 15 μL, recovered PCR product DNA: 40 ng, recovered plasmid: 20 ng; after a 30-minute incubation at 42° C., transform it into *Escherichia coli*.

```
pAAV8-590-7 aa-F:
                                   SEQ ID NO: 5
AGGACCCTGTTACCGCCAAC, set forth in pAAV8-590-7 aa-R:
                                   SEQ ID NO: 6
GATGTTTCAGGCCAAAGCCG, set forth in
```

Figure 1:
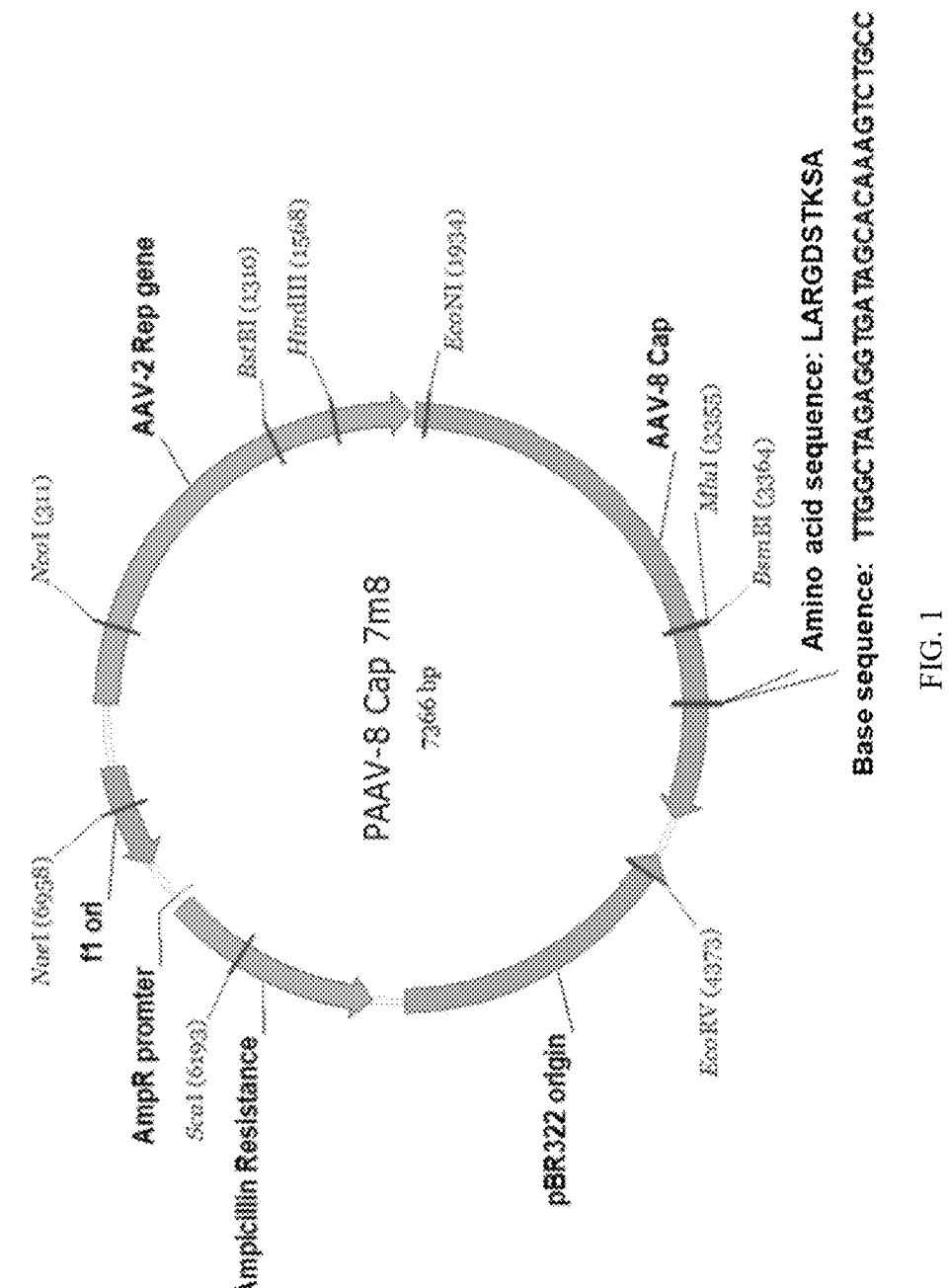
FIG. 1 shows a schematic representation of the AAV8-590RGD vector in Embodiment 1 of the present invention, where amino acid sequence is LARGDSTKSA (SEQ ID NO: 3), base sequence is ttggctagaggtgatagcacaaagtctgcc (SEQ ID NO: 4).

As shown in FIG. 1, said constructed pAAV8-590RGD vector structure comprising the benzyl resistance gene, AAV replication genes, and the AAV8 capsid gene, the resistance gene coding for ampicillin, the AAV replication gene, and the AAV8 capsid gene, which contains a random base sequence corresponding to a 10-amino acid sequence: LARGDSTKSA, set forth in SEQ ID NO: 3.

Embodiment 2: AAV Virus Packaging (I) Cryopreservation of AAV-293 Cells

With the increase of passage times, AAV-293 cells will have a decline in growth status, mutations, etc. In order to prevent such phenomena, we need to cryopreserve cells in large quantities at the beginning to ensure the stability and continuity of the experiment. Cryopreservation was performed in the logarithmic growth phase to increase the survival rate of cell resuscitation.

1. Remove the cell culture supernatant and add PBS to wash off residual medium;

2. Add 0.25% pancreatic enzyme, digest for 1-2 min, when the cells become round and the intercellular space increased under the microscope, remove the pancreatic enzyme, add fresh medium to mix well, then move said fresh medium into a centrifuge tube.

3. Cell counting: shake all the cells, add 3 mL of 10% DMEM pre-warmed at 37° C., pipette said cells with a 10 mL pipette, pipette said cells for 6 to 8 times with greater force, without leaving dead ends. After that, all the cells are sucked out and placed in a 15 mL centrifuge tube. 50 μL of the mixed cells are placed in a 1.5 mL eppendorf tube, and 450 μL of 10% DMEM is added, which is a 10-fold dilution, mixed, and 10 μL of the cells are counted in a counting plate. There are four large cells on the counting board, each with 16 small cells. For counting, all four large cells are counted, the total number is divided by 4 (to obtain the number of cells per large cell), and multiplied by 10 (10-fold dilution), which is the actual n million/mL cell concentration.

4. Centrifuge the cells at 1000 rpm for 5 minutes. Remove the supernatant.

5. According to the cell counting, add cell cryopreservation medium (70% complete medium+20% FBS+10% DMSO) to resuspend said cells at a density of 3×106 pcs/mL.

6. Divide said cells into cell cryopreservation tubes, then place it into a cryopreservation box, and put it into an ultra-low temperature refrigerator at −80° C.

7. The next day, place the cells in a liquid nitrogen tank for long-term storage and record. During the preservation process, it is necessary to resuscitate cells from time to time to detect cell survival rate and observe the status of cells.

(II) Passaging of AAV-293 Cells

When the cell growth reaches 80%-90% confluency, it is necessary to passage the cells to expand the number of cells and maintain a good growth status of cells.

1. Digest the cells using the same method as for cell freezing.

2. After cell centrifugation, add complete culture medium and resuspend said cell.

3. According to the specific situation, divide the cells into 10 cm dishes, and each dish is supplemented to 10 mL of medium.

(III) Resuscitation of AAV-293 Cells

When said cells are passaged too many times, said state of the cells becomes worse, or a contamination incident occurs, it is necessary to discard said cells and revive the initially cryopreserved cells.

1. Set water bath at the temperature of 37-42° C.

2. Check the cell bank records, take out the cryopreserved cells from the liquid nitrogen tank according to the records (wear cotton gloves to prevent frostbite), quickly throw said cryopreserved cells into the water bath and shake quickly, and try to completely dissolve said cell solution within 1 to 2 min.

3. Transfer the cell suspension to a 15 mL centrifuge tube, add 1 mL of fresh complete culture medium, mix thoroughly and centrifuge at 1000 rpm/min for 5 min.

4. Remove the supernatant, add 5 mL of fresh complete culture medium, mix thoroughly to precipitate, and then transfer to a 6 cm culture dish.

5. Place the culture dish smoothly into an incubator at 37° C., 5% CO2 and 95% relative humidity for culture.

6. Observe the cell survival rate on the next day. Replace the culture medium for the cells and continue to monitor their growth daily thereafter.

(IV) AAV Packaging and Concentration

1. Plasmid Amplification

The constructed AAV vector, packaging plasmid, and adjuvant plasmid need to be extracted in large quantities, to be suitable for virus packaging with the concentration greater than 1 µg/µL and the A260/280 ratio between 1.7 and 1.8. It is recommended to use the Qiagen large-scale plasmid purification kit for large-scale endotoxin-free plasmid extraction.

2. Transfecting AAV-293 Cells

Aspirate the medium from the T75 flask containing AAV-293 cells. Add 2 mL of 0.25% trypsin (pre-cooled at 4° C.) to evenly cover the bottom of the flask. Place it in a 37° C. incubator for 3-5 minutes. Remove the flask and gently shake to detach the cells from the bottom. Transfer all cells to a 15 mL centrifuge tube. Add 3 mL of pre-warmed 10% DMEM to the tube. Use a 10 mL pipette with the pipettor to blow, applying moderate force and blowing 6-8 times. For the area near the flask's neck, aim the pipette tip and gently pipette to cover the cells near the neck. Centrifuge the cells at 1000 rpm/min for 5 minutes. Remove the supernatant, add 5 mL of fresh 10% DMEM, mix well, and transfer the cells to a T75 flask. Add 10 mL of 10% DMEM medium to each T75 flask. On the day of transfection (designated as day one), count the cells. For transfection on the second day, plate 900-1000,000 cells per T75 flask. For transfection on the third day, plate 350-400,000 cells per T75 flask. The cell density should be 80-90% at the time of transfection. No medium change is required before transfection.

3. Lipofection Complex Formation

Reagents Amount

Plasmid Vector 5 µL (1.0 µg/µL)

Packaging Plasmid 5 µL (1.0 µg/µL)

Helper Plasmid 5 µL (1.0 µg/µL)

Note: Lipofiter™ transfection reagent is a product of Hanheng Biologicals. Please refer to the Lipofiter™ manual for usage instructions.

4. AAV Virus Collection:

Viral particles are present in both packaging cells and culture supernatant. Collecting both cells to obtain the best yield.

1) Prepare a dry ice ethanol bath (pour ethanol into a foam box with dry ice; liquid nitrogen can be used instead of the dry ice ethanol bath) and a 37° C. water bath.

2) Collect the virus-producing cells along with the culture medium into a 15 mL centrifuge tube. Tilt the culture dish at a certain angle to scrape the cells into the medium.

3) Centrifuge at 1000 rpm for 3 minutes to separate cells and supernatant. Set aside the supernatant and resuspend cells in 1 mL PBS.

4) Transfer the cell suspension back and forth between the dry ice ethanol bath and the 37° C. water bath, freeze and thaw four times. Shake gently after each thaw. Note: each freezing and thawing cycle takes about ten minutes.

5. AAV Virus Concentration:

1) Centrifuge at 10,000 g to remove cell debris. Transfer the supernatant to a new centrifuge tube.

2) Combine the supernatants collected twice, filter impurities using a 0.45 µm filter.

3) Add an equal volume of 1M NaCl and 10% PEG8000 solution, mix well, and incubate overnight at 4° C.

4) Centrifuge at 12,000 rpm for 2 hours, discard the supernatant, dissolve the virus pellet in an appropriate volume of PBS solution. After complete dissolution, filter the solution using a 0.22 µm filter to sterilize.

5) Add Benzonase nuclease to digest and remove residual plasmid DNA (final concentration: 50 U/mL). Close the cap and invert several times to mix thoroughly. Incubate at 37° C. for 30 minutes.

6) Filter through a 0.45 µm filter, the filtrate is the concentrated AAV virus.

6. AAV Purification

1) Add solid CsCl to the virus concentrate until the density reaches 1.41 g/mL (refractive index 1.372).

2) Place the sample in an ultracentrifuge tube and fill the remaining space in the tube with a pre-made 1.41 g/mL CsCl solution.

3) Centrifuge at 175,000 g for 24 hours to form a density gradient. Sequentially collect samples of different densities and determine the titer of each sample. Collect the fraction enriched with AAV particles.

4) Repeat the above process once.

5) Load the virus into a 100 kDa dialysis bag, and dialyze at 4° C. overnight. This is the purified AAV virus.

AAV Virus Titration (Using Q-PCR)

1) Take 20 μL of the concentrated virus and add 1 μL RNAse-free DNAse, mix, and incubate at 37° C. for 30 minutes.

2) Centrifuge at 4° C., 12,000 rpm for 10 minutes. Transfer 10 μL of the supernatant to another sterile 1.5 mL EP tube.

3) Add 90 μL of Dilution Buffer (1 mM Tris-HCl, pH 8.0, 0.1 mM EDTA, 150 mM NaCl), mix, and incubate at 37° C. in a water bath for 30 minutes.

4) Cool to room temperature, add 1 μL proteinase K, and incubate at 65° C. in a water bath for 1 hour.

5) Incubate at 100° C. in a water bath for 10 minutes, then cool to room temperature.

6) Perform Q-PCR to determine the titer.

Storage and Dilution of AAV Virus

1. Virus Storage:

Upon receiving the virus, use it for experiments within a short period, and store it temporarily at 4° C. For long-term storage, place it at −80° C. (store the virus in cryovials and seal with parafilm).

1) Viruses can be stored at −80° C. for more than 6 months. However, if the virus storage time exceeds 6 months, it is recommended to re-measure the virus titer before use.

2) Repeated freeze-thaw cycles will decrease the virus titer: each cycle reduces the titer by 10%. Therefore, during virus use, avoid repeated freeze-thaw cycles as much as possible. To prevent this, it is recommended to aliquot the virus upon receipt according to the amount needed for each use.

2. Virus Dilution:

If you need to dilute the virus, take it out and thaw it on ice. Use PBS buffer or serum-free culture medium for target cells (serum or double-antibody-containing media do not affect virus infection). After mixing, store at 4° C. (use within three days) after aliquoting.

Safety Precautions for AAV Use

1. It is advisable to use a biological safety cabinet when working with viruses. If using a regular laminar flow cabinet, do not turn on the exhaust fan.

2. Wear lab coats, masks, and gloves when handling viruses.

3. Be especially careful not to generate aerosols or splashes when working with viruses. If there is virus contamination in the laminar flow cabinet, immediately clean it with a 70% ethanol and 1% SDS solution. Items that have come into contact with the virus, such as pipette tips, centrifuge tubes, culture plates, and medium, should be soaked in 84 disinfectant or 1% SDS overnight before disposal.

4. When observing cell infection under a microscope, follow these steps: tighten the culture bottle or cover the culture plate. Clean the outer wall of the culture bottle with 70% ethanol before moving to the microscope for observation and photography. Before leaving the microscope workstation, clean the microscope workstation with 70% ethanol.

5. If centrifugation is required, use well-sealed centrifuge tubes or seal the tubes with parafilm before centrifugation. Whenever possible, use a centrifuge located inside a tissue culture room.

6. After removing gloves, wash your hands with soap and water.

Embodiment 3: AAV Capsid-Packaged Virus with Random Sequences, Mouse Vitreous Cavity Injection, and Retina Extraction 1. Anesthesia: 0.01 mL/g of 4.3% hydrated chloral hydrate.

2. Pupil dilation: dilate the pupil and maintain ocular surface moisture with methylcellulose.

3. Adjust mouse head pPosition, and injection site: approximately 1 mm behind the corneal edge.

4. Incision: make an incision using a 33G syringe needle. Insert the needle tip vertically and then tilt it. Slowly inject AAV capsid-packaged viruses containing specific amino acid sequences into the mouse vitreous cavity. After injection, keep the needle in place for 0.5-1 minute, then withdraw it quickly.

5. Approximately one week later, euthanize the mice under anesthesia. Extract the target tissues, including the retina and retinal pigment epithelium. Extract genomic DNA and conduct sequencing analysis of the AAV capsid sequences that have penetrated the target tissue.

Figure 2:
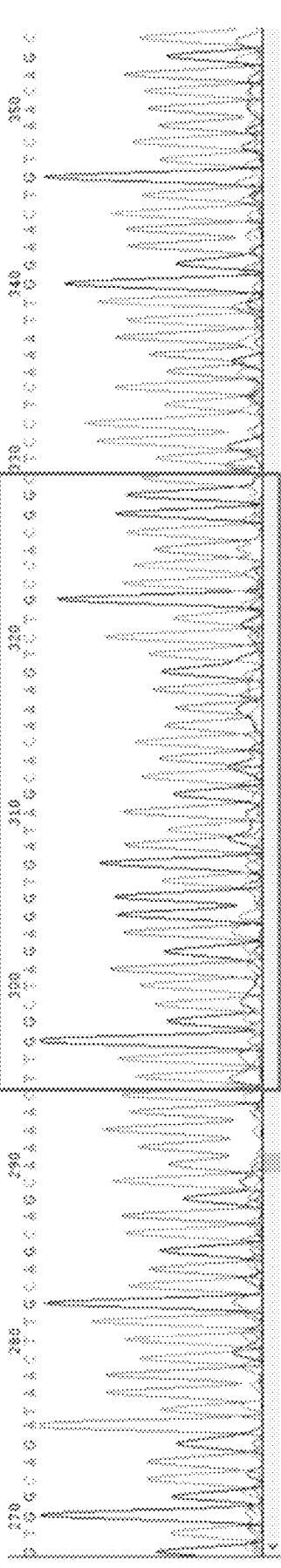
FIG. 2 shows the AAV8-590RGD serotype base sequencing results screened in Embodiment 3 of the present invention, where gtggcagataacttgcagcagcaaaacttggctagaggtgatagcacaaagtctgccacggctcctcaaattggaactgtcaacagc (SEQ ID NO: 7) is shown.
Figure 3B:
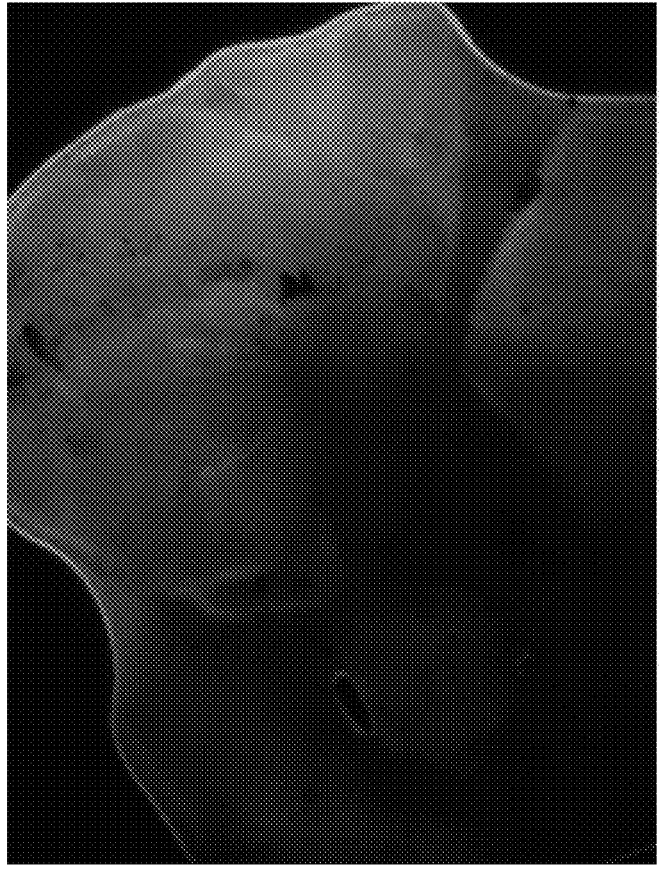
Figure 3A:
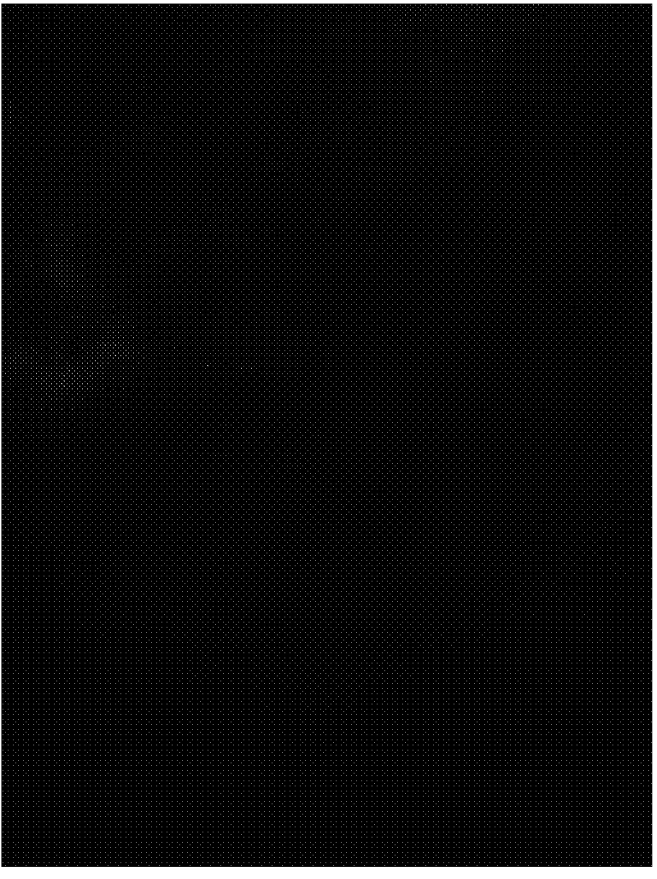
Figure 4B:
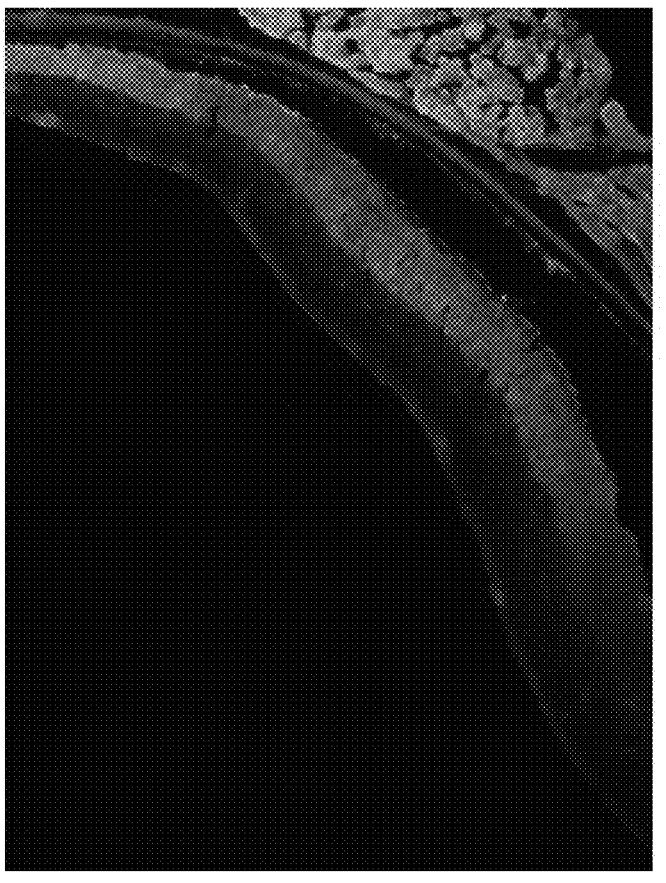
Figure 4A:
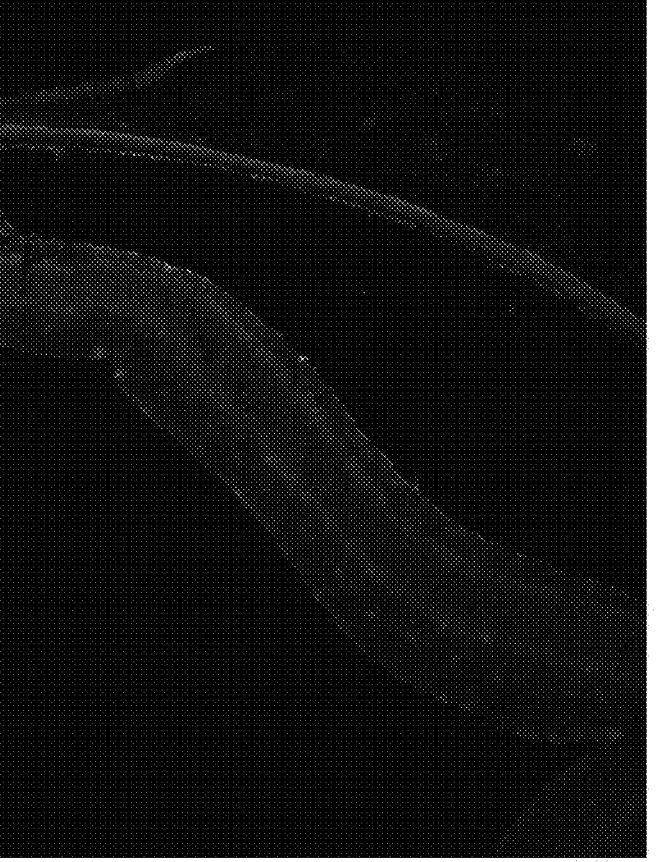
Figure 5A:
Figure 5A:
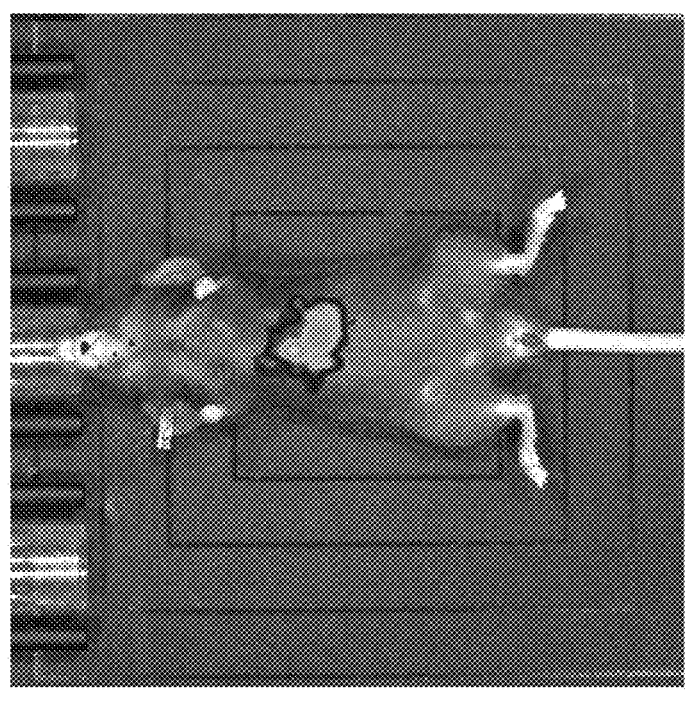
Figure 5A:
Figure 5A:
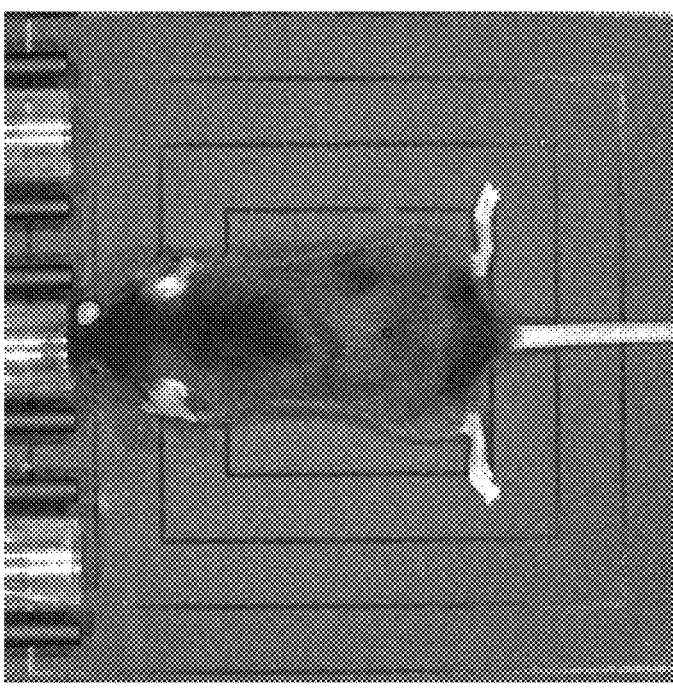
Figure 5B:
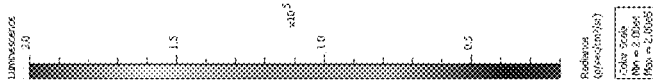
Figure 5B:
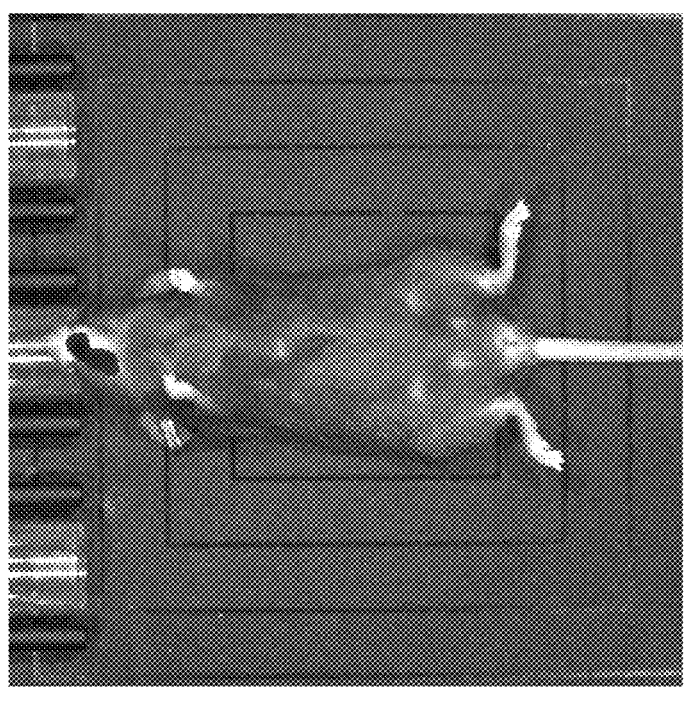
Figure 5B:
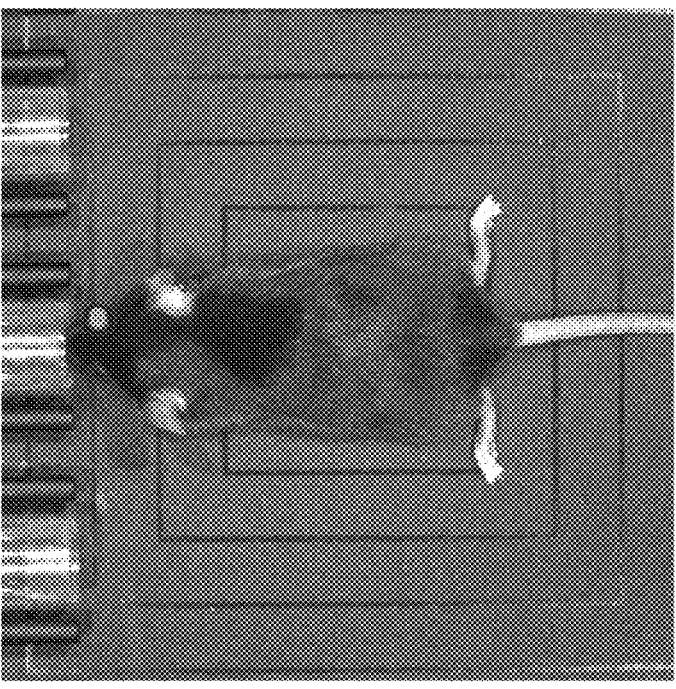
Figure 6B:
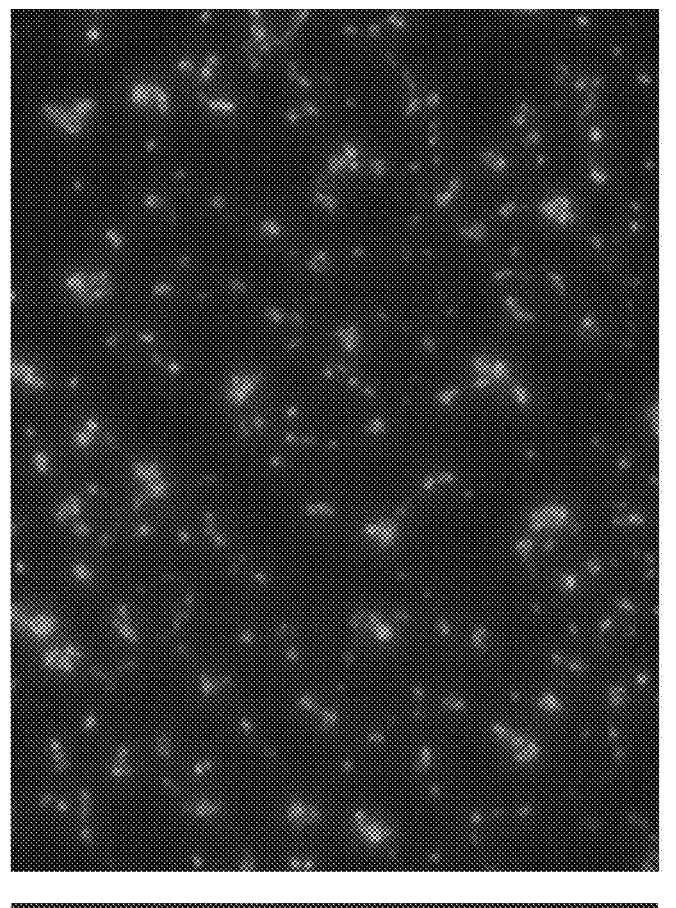
Figure 6A:
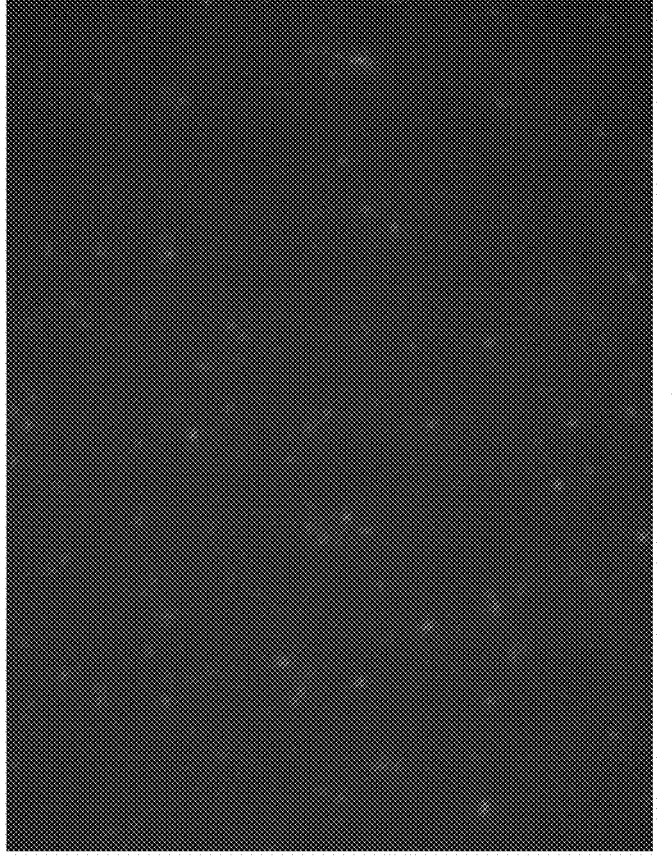
Figures 7A, 7B:
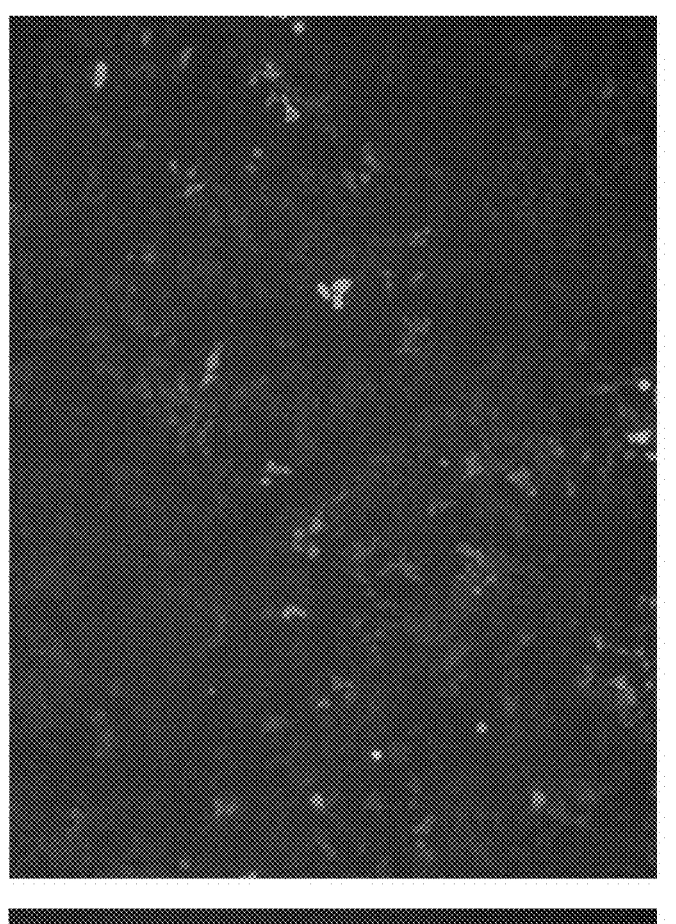
Figure 8B:
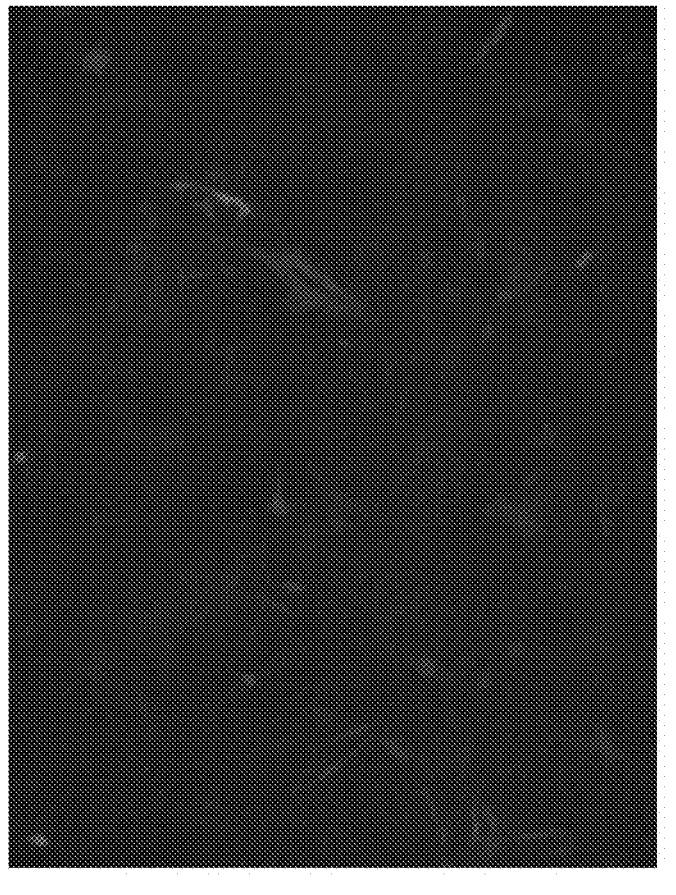
Figure 8A:
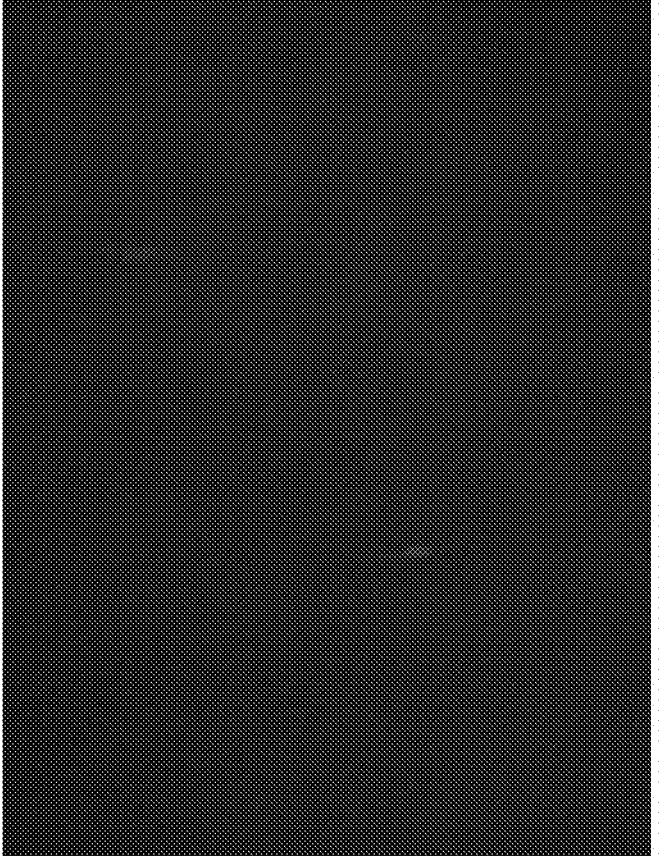
Figure 9B:
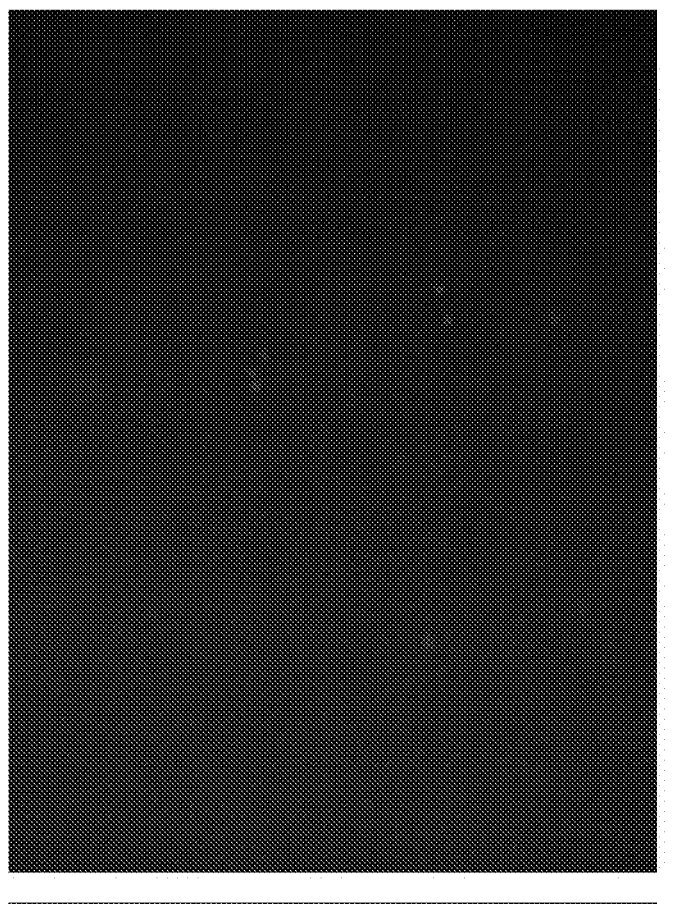
Figure 9A:
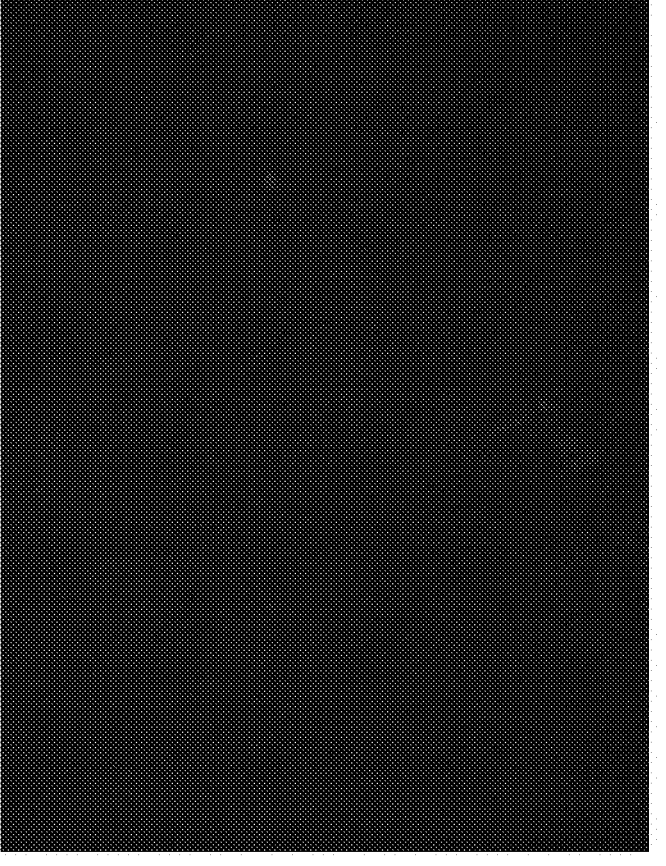
Figure 10B:
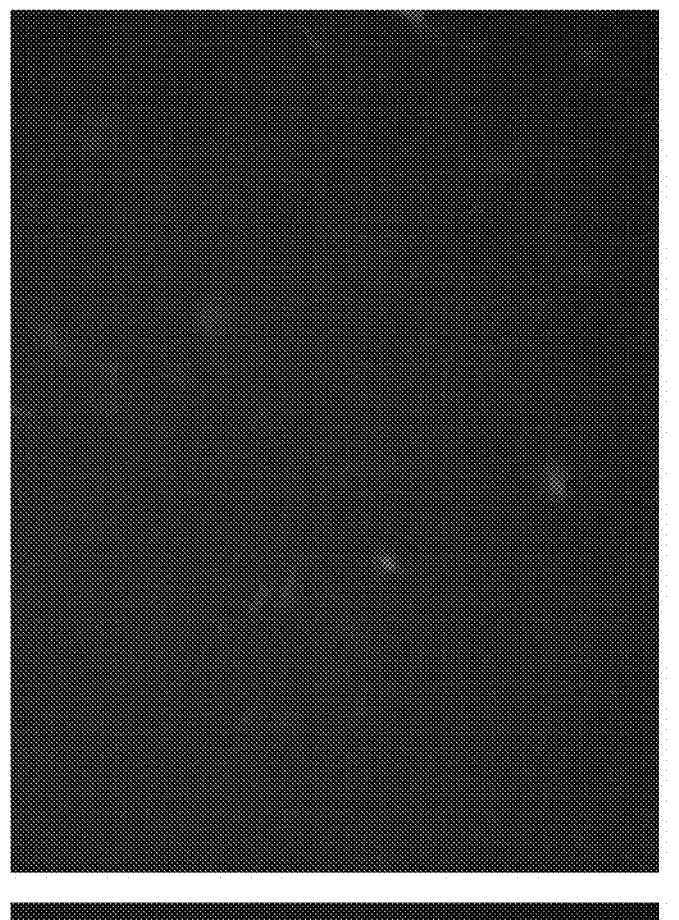
Figure 10A:
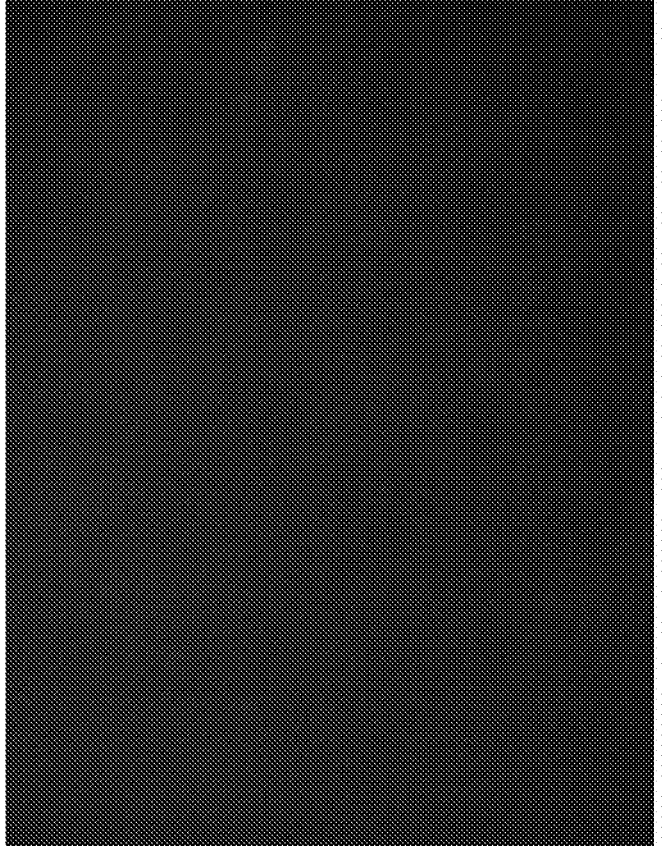
Figure 11B:
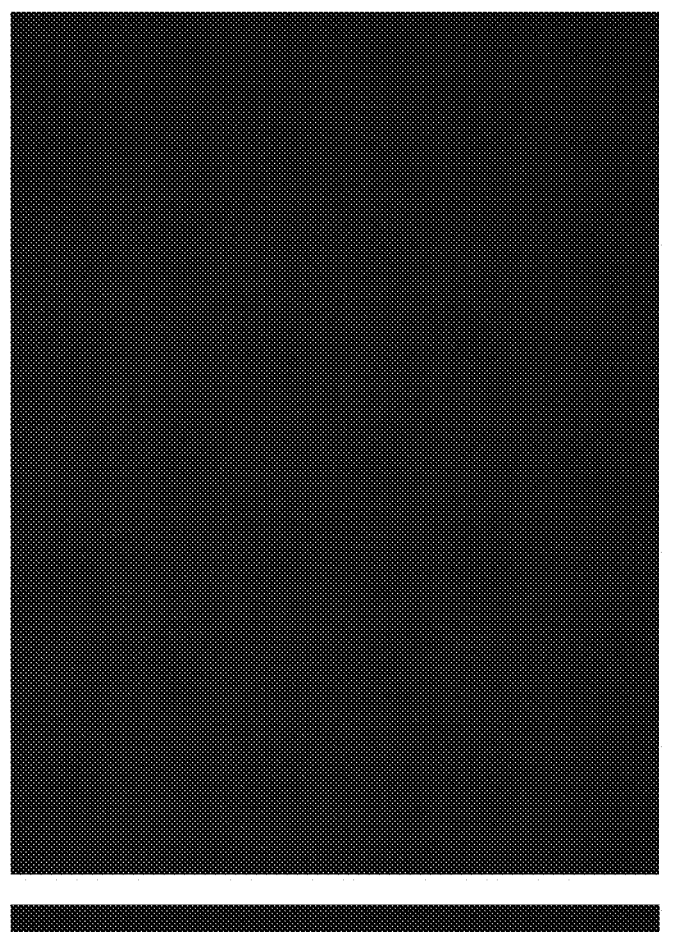
Figure 11A:
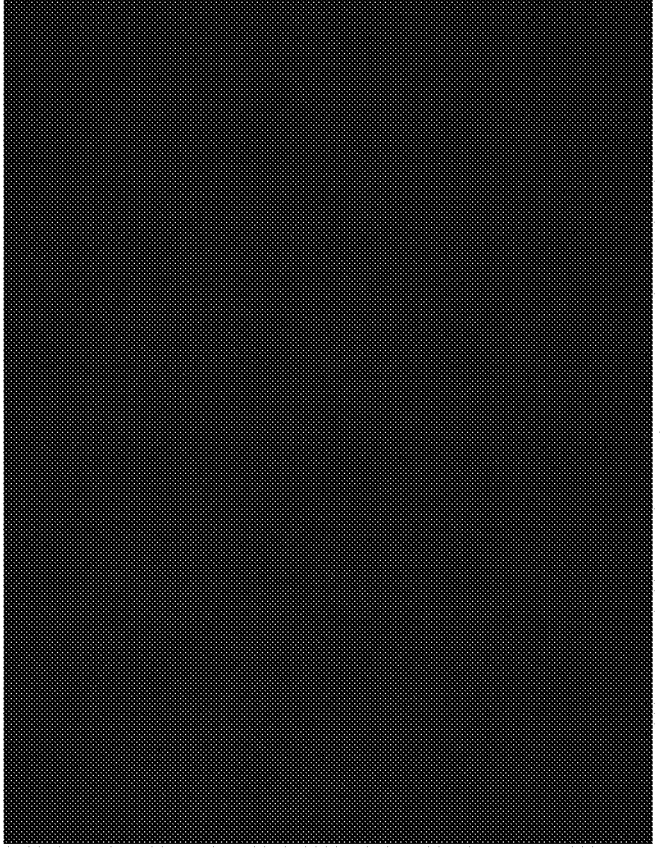
Figure 12B:
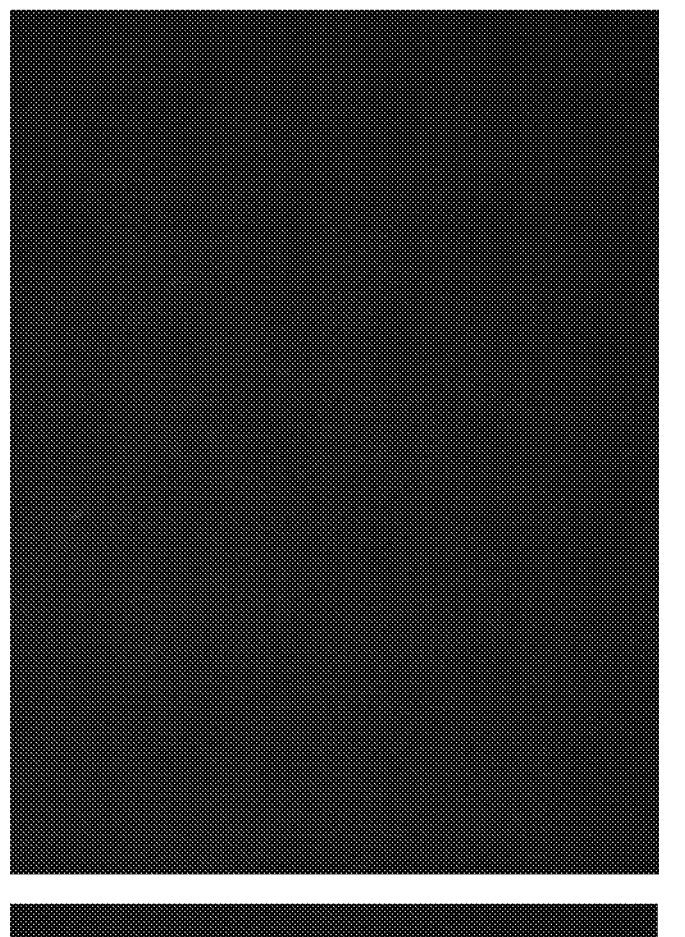
Figure 12A:
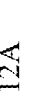

Analyze the AAV sequences contained in the genome based on the sequencing results (see FIG. 2). The boxes represent the inserted sequences obtained from sequencing, consisting of a total of 30 bases with 21 random bases. Among these, the sequencing result shows a prominent peak in the 21 random base sequences, and the read analysis reveals the base sequence as "ttggctagaggtga-tagcacaaagtctgcc".

Embodiment 4: Viruses Packaged with AAV-8 and AAV8-590RGD Capsids, Cell Infection, and Fluorescence Comparison 1. Cell retrieval: locate the specific cells needed in the cell repository table.

2. Thawing cells: retrieve cells from the liquid nitrogen tank and quickly place them in a 37-degree water bath while gently shaking.

3. Centrifugation: place the cryogenic tube with fully melted internal liquid in a centrifuge at 800 RPM for 5 minutes.

4. Remove supernatant: after centrifugation, discard the supernatant from the centrifuge tube.

5. Cell resuspension: add 1 mL of the corresponding culture medium to the cryogenic tube, gently pipette to obtain a single-cell suspension.

6. Prepare culture Dish: take an appropriate-sized dish (usually 10 cm or 6 cm), add culture medium.

7. Add cell suspension: add the evenly pipetted cell suspension from the cryogenic tube to the dish.

8. Uniform mixing: shake the cell culture dish gently in a rice grain motion to ensure even mixing.

9. Incubation: place the well-mixed cell culture dish in a 37-degree incubator.

10. Next day: remove the dish and observe under a microscope, perform subsequent operations like medium change, etc.

11. Cell harvesting: retrieve cells at 80% confluency from the incubator.

12. Remove old medium: aspirate the original culture medium from the dish.

13. Add PBS wash: add 3 mL of PBS buffer, shake the dish evenly to allow PBS to reach every corner.

14. Remove PBS: discard the PBS used for washing.

15. Add Trypsin: add 1 mL of trypsin, shake the dish evenly to ensure trypsin contacts every corner.

16. Return to incubator: place the dish back in the 37-degree incubator.

17. Digestion: digest for a certain period (usually between 1 to 2 minutes). Remove the cell dish.

18. Check for cell detachment: hold the dish with your left hand and gently tap along the wall of the dish with your right hand. Cells slipping off indicate proper digestion.

19. Alternate confirmation: cell rounding under a microscope is another indicator of successful digestion.

20. Terminate digestion: add 2 mL of the appropriate culture medium to stop digestion in a 10 cm dish.

21. Evenly shake: gently shake the dish with termination solution.

22. Cell suspension: use a 1 mL pipette to pipette the cells, making them into a single-cell suspension.

23. Transfer to centrifuge tube: after pipetting, transfer all the liquid to a 5 mL centrifuge tube.

24. Centrifugation: label the centrifuge tube and place it in a centrifuge at 800 RPM for 5 minutes.

25. Remove supernatant: after centrifugation, discard the supernatant from the centrifuge tube.

26. Resuspend cells: add 2 mL of the appropriate culture medium to resuspend the cells into a single-cell suspension.

27. Cell plating: plate cells into multi-well plates based on a specified number.

28. Mixcells: mix cells with the culture medium in the multi-well plates.

29. Incubation: place the multi-well plates in a 37-degree incubator.

30. Day before infection: plate cells in multi-well plates (refer to the previous steps).

31. Infection: infection can be carried out 12 hours after cell plating.

32. 12 hours after cell plating, prepare the respective virus/sodium butyrate.

33. Prepare virus: mix the appropriate amount of virus with 2% serum-containing medium based on the cell's corresponding MOI value.

34. Add sodium butyrate: add sodium butyrate at a 1:1000 ratio.

35. Change medium: change the medium to 2% serum-containing medium.

36. Add virus-sodium butyratemixture: add the virus-sodium butyrate mixture to the multi-well plates and shake well.

37. Incubation: place the multi-well plates in a 37° C. incubator.

38. 6 Hours after incubation: after 6 hours of incubation, remove the multi-well plates and aspirate all the liquid inside.

39. Add fresh medium: add an appropriate amount of fresh culture medium and place it back in a 37° C. incubator.

40. Fluorescence imaging: after a certain period, capture fluorescence images and submit the samples.

FIGS. 6A-15B represent the fluorescence observed in cells infected with viruses packaged with AAV-8 (A) and AAV8-590RGD (B) capsids, containing the same virus load. The cells include retinal ganglion cells (FIGS. 6A-6B), Neuro2A cells (FIGS. 7A-7B), U251 cells (FIGS. 8A-8B), ARPE-19 cells (FIGS. 9A-9B), SH-SY-5Y cells (FIGS. 10A-10B), BV2 cells (FIGS. 11A-11B), HBMEC primary isolated cells (FIGS. 12A-12B), JURKAT cells (FIGS. 13A-13B), K562 cells (FIGS. 14A-14B), and THP1 cells (FIGS.

Figure 13B:
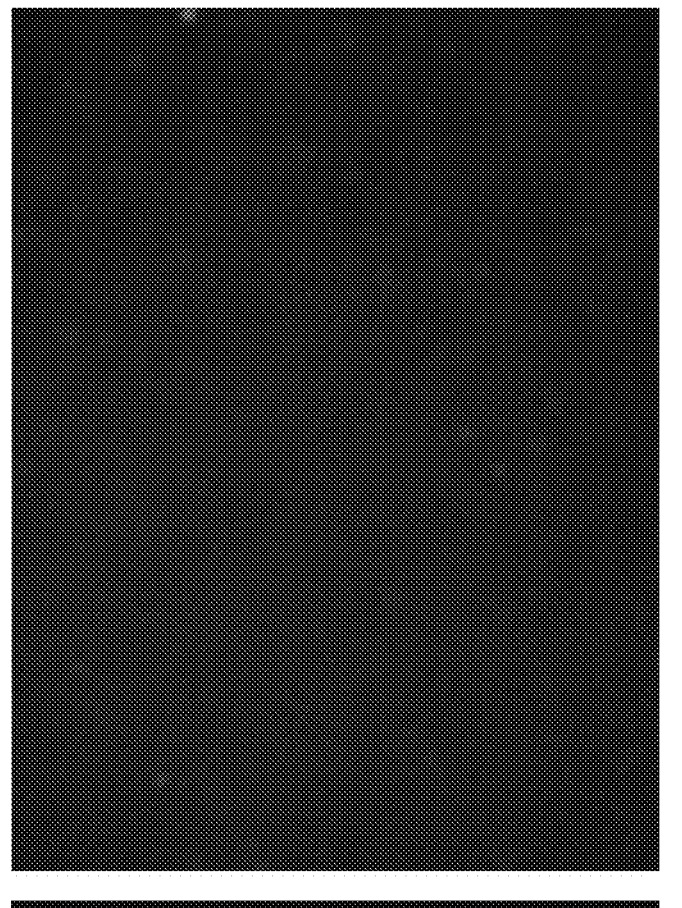
Figure 13A:
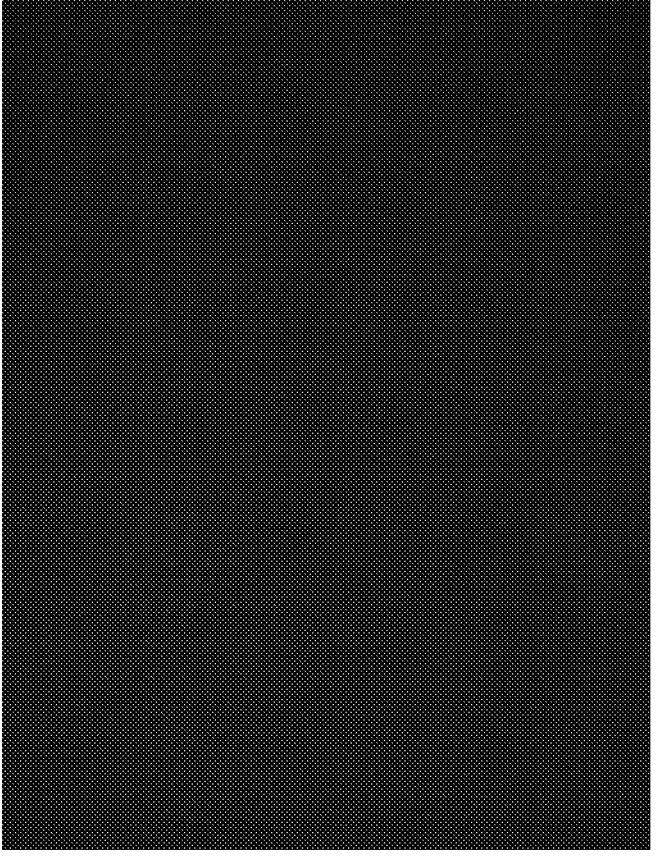
Figure 14B:
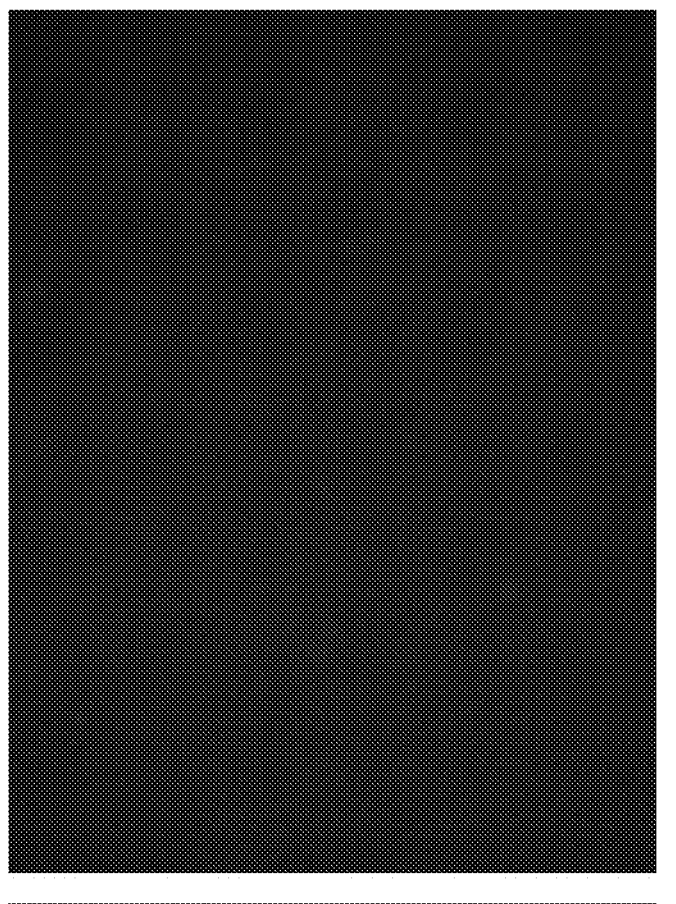
Figure 14A:
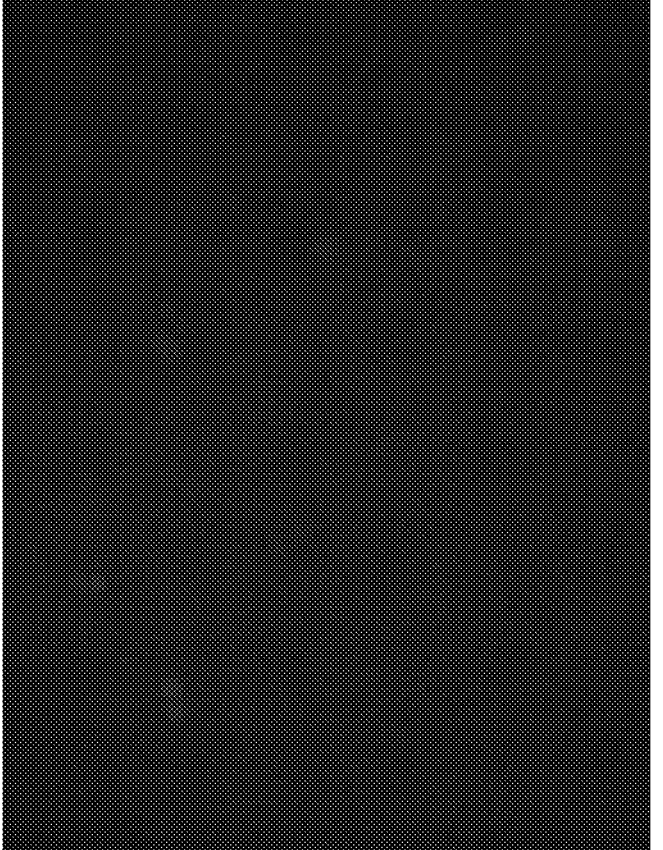
Figure 15B:
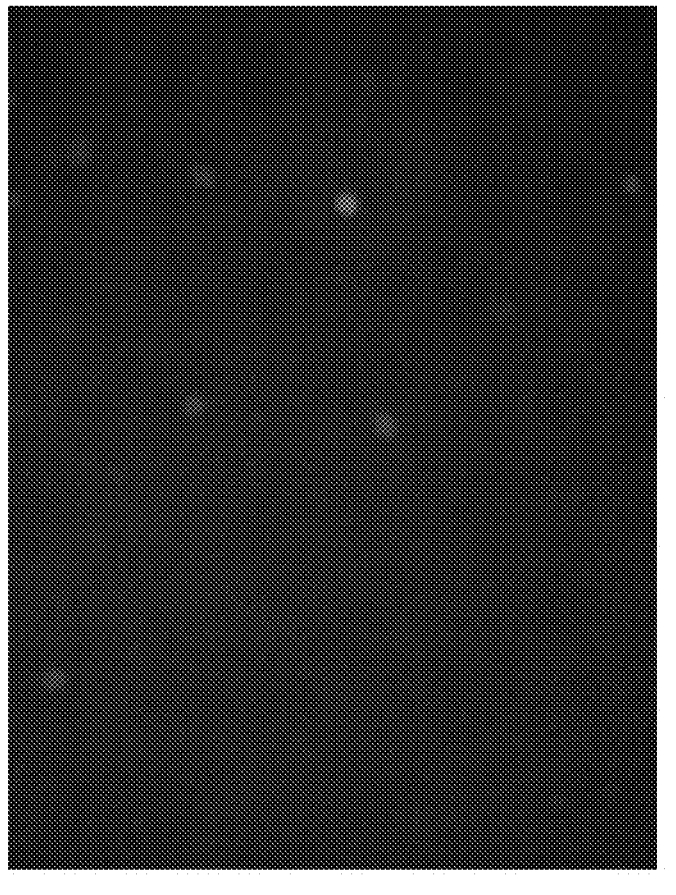
Figure 15A:
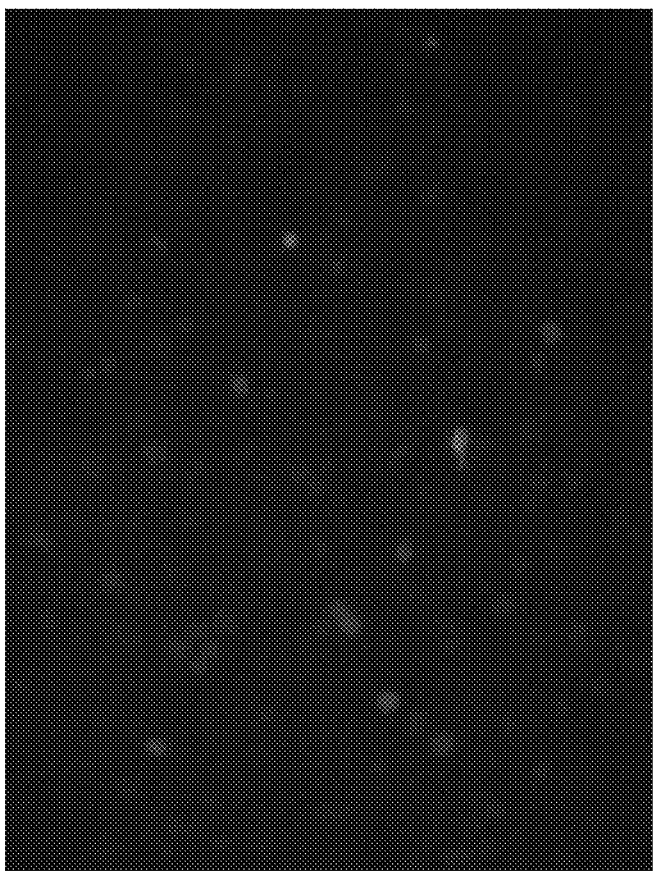

15A-15B). AAV8-590RGD capsid-packaged viruses exhibit better infection efficiency than AAV-8 capsid-packaged viruses in retinal ganglion cells (FIGS. 6A-6B), Neuro2A cells (FIGS. 7A-7B), U251 cells (FIGS. 8A-8B), SH-SY-5Y cells (FIGS. 10A-10B), HBMEC primary isolated cells (FIGS. 12A-12B), and JURKAT cells (FIGS. 13A-13B).

Embodiment 5: Comparison of Viral Infection Areas Through Intravitreal and Brain Stereotaxic Injections of AAV-8 and AAV8-590RGD Encapsulated Viruses (I) Intravitreal Injection (Refer to Embodiment 3)

(II) Stereotaxic Injection in Mouse Brain Steps:

1. Anesthesia

1) Administer anesthesia to the mouse using anesthetics such as pentobarbital sodium, chloral hydrate, or a mixture of isoflurane/oxygen. Ensure moderate anesthesia level.

2. Fixation

1) Provide illumination using a cold light source. Secure the anesthetized mouse on the brain stereotaxic injection apparatus.

2) Secure the skull: insert one ear bar gently into the external auditory canal, fix it against the bony external auditory canal floor, then insert another ear bar similarly. Check the stability of the mouse's head fixation, ensure no tilting, and symmetrical scale on both ear bars. Adjust the ear bars slightly to align both scales evenly and centralize the head completely.

3) Secure the upper jaw: insert the mouse's upper incisors into the groove of the upper teeth fixation plate, and tighten the screw. Apply pressure from various directions on the animal's head, and there should be no movement. Adjust the anterior and posterior fontanelles to be on the same sagittal line using the positioning needle, ensuring Bregma and Lambda are at the same horizontal plane as much as possible.

3. Drilling

1) Shave the fur on the mouse's head using a pet shaver and disinfect the head with medical alcohol and iodine.

2) Apply eye ointment to keep the eyes moist and prevent blindness due to dryness during the procedure.

3) Use medical scissors to cut the scalp from the midline between the eyes to the roots of both ears.

4) Use hemostatic forceps to enlarge the opening. Wipe and remove the surface dura mater with a cotton swab soaked in hydrogen peroxide.

5) Ensure Bregma (X=0, Y=0, Z=0) and Lambda are on the same horizontal plane (difference between X and Z values should be less than 0.1) using the positioning device.

6) Determine the position parameters of the brain area to be injected based on the brain atlas.

7) Use the positioning device to locate the virus injection site and mark it on the skull using a marker pen.

8) Gently grind the skull at the injection site with a skull drill. Slowly thin the skull until a crack appears; then, carefully pierce it with the needle of a medical syringe to avoid damage.

4. Virus Injection

1) Rinse the microinjection needle (5 μL) with PBS 3-5 times.

2) Draw about 1 μL of air, then draw about 1 μL of diluted virus. Test if the syringe is unobstructed in the air.

4) Assemble the microinjection pump and needle, position it above the drilled hole with the needle parallel to the skull (Z=0), adjust the position of the syringe to match the previous drilling position.

4) Slowly lower the injection needle according to the predetermined depth.

5) Inject the virus at a speed of 0.05 μL/min. Stop the injection when only 0.5 μL is left.

6) After injection, leave the injection needle at the injection site for 10 minutes to allow virus diffusion, then slowly retract the needle.

7) Rinse the microinjection needle with PBS 5 times for later use.

8) If bleeding occurs during injection, immediately absorb it with a cotton swab to prevent virus carryover.

5. Suturing

1) Suture the scalp after removing the injection needle completely.

2) After the experiment, place the mouse in a suitable environment (around 25° C., such as on a constant temperature heating plate) for recovery. Return the mouse to the cage when it regains consciousness.

6. Detection

1) Sacrifice the mice infected with the virus 3-4 weeks after injection. Fix the brain in 4% paraformaldehyde for about 1 day, then dehydrate in 20% and 30% sucrose solutions.

2) Freeze section the brain, thickness 10 μm. Observe the fluorescence under a fluorescence microscope.

Figure 16B:
Figure 16A:
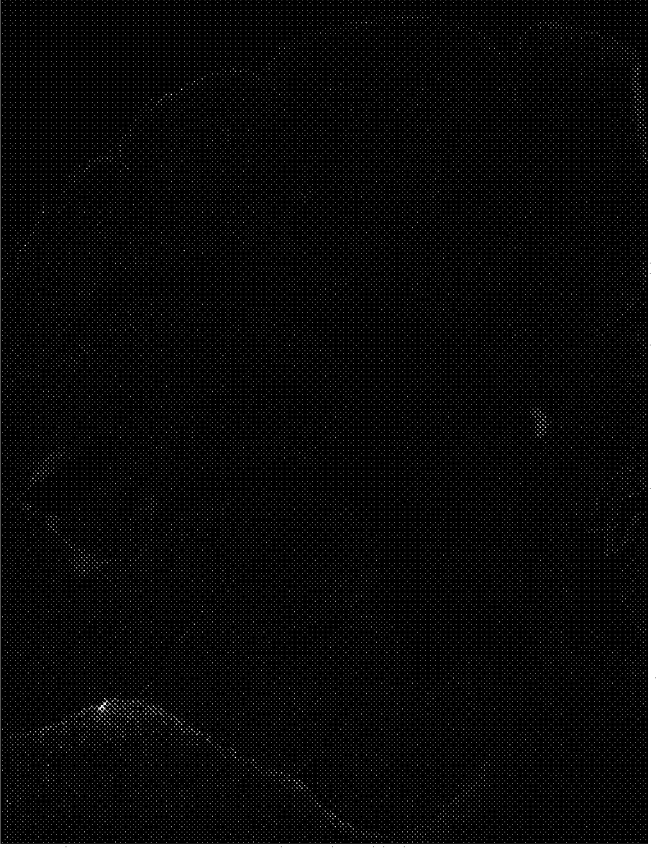
Figure 17B:
Figure 17A:
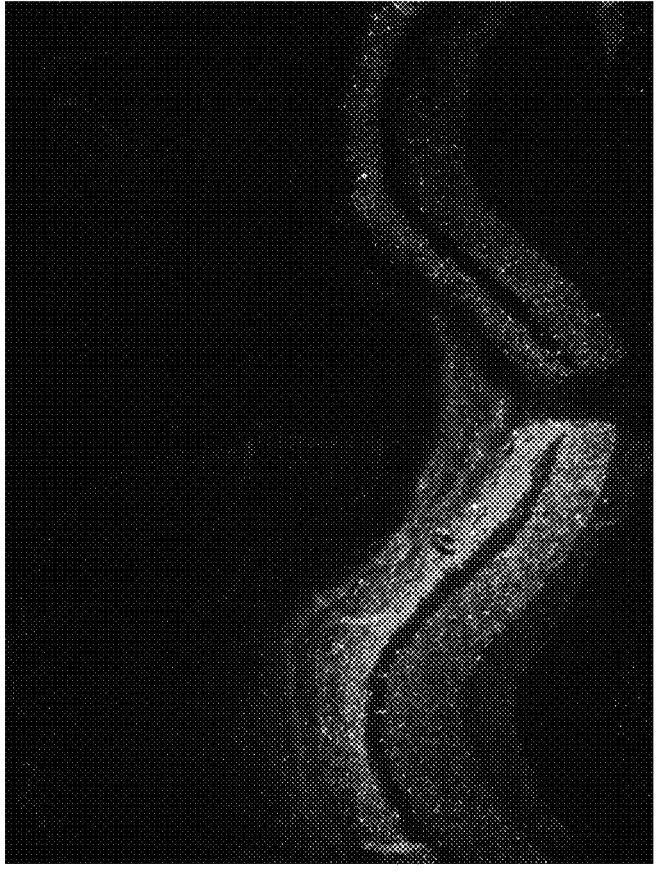
Figure 18B:
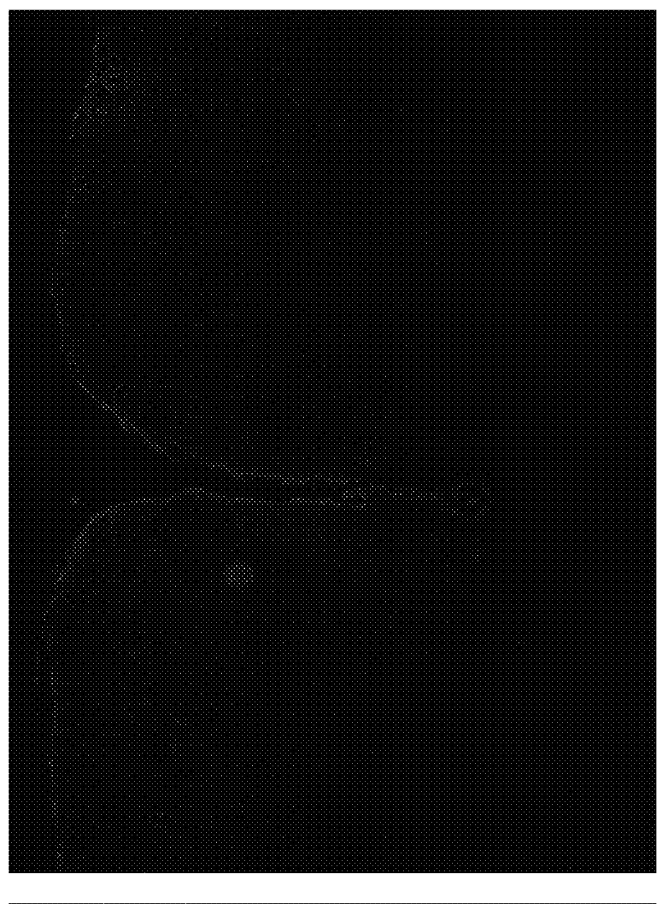
Figure 18A:
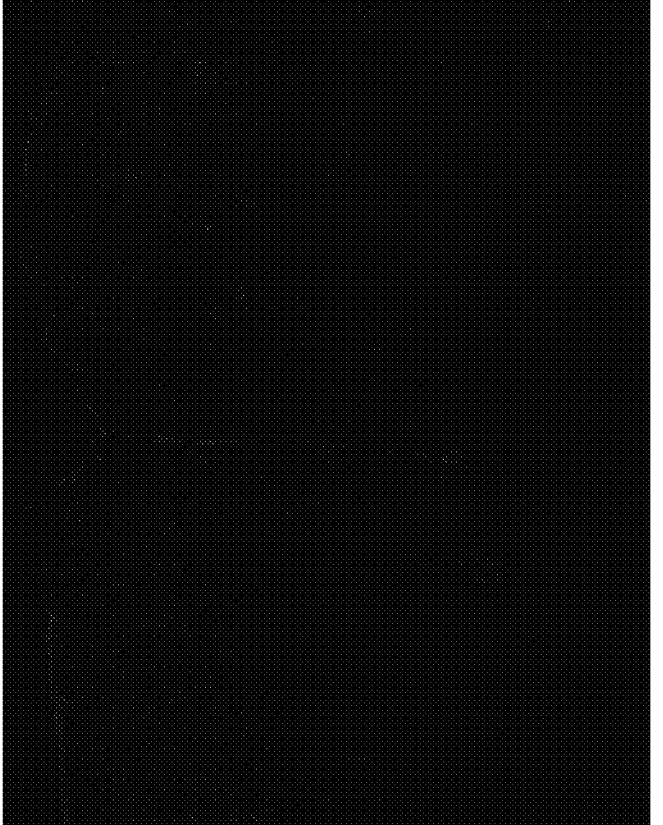
Figure 19B:
Figure 19A:
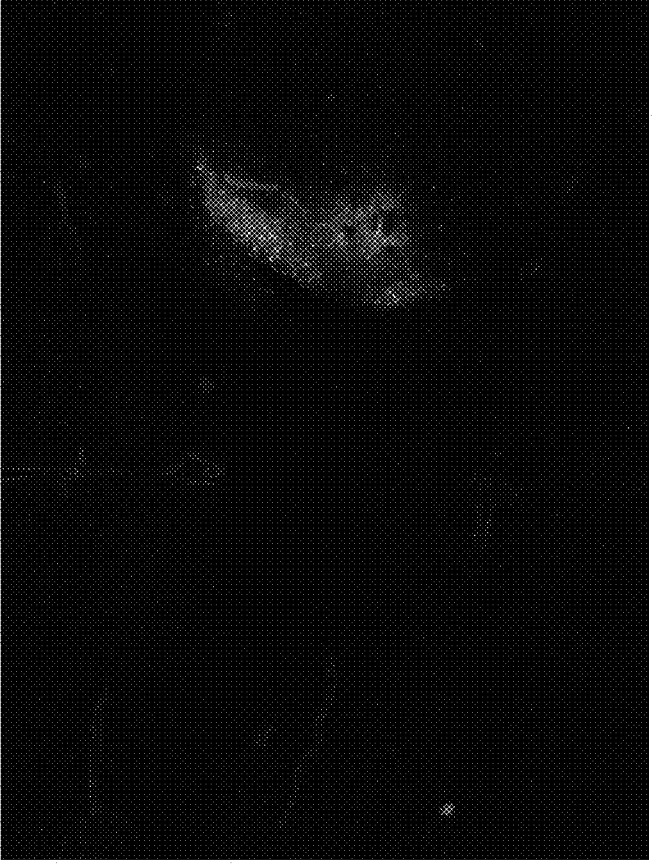

FIGS. 3A-3B, FIGS. 4A-4B, and FIGS. 5A-5B represent the expression results observed through intravitreal injection, retinal cup bodies (FIGS. 3A-3B), retinal frozen sections (FIGS. 4A-4B), and live imaging (FIGS. 5A-5B) using AAV-8 (A) and AAV8-590RGD (B) encapsulated viruses at the same viral dose. It was found that the virus encapsulated with AAV8-590RGD capsid had better infection efficiency and lower organ leakage. The brain stereotaxic injection infected mouse cerebellum (FIGS. 16A-16B), mouse hippocampus (FIGS. 17A-17B), mouse motor cortex (FIGS. 18A-18B), and mouse striatum (FIGS. 19A-19B) were observed for fluorescence. AAV8-590RGD encapsulated virus showed better infection efficiency than AAV-8 encapsulated virus in the mouse cerebellum (FIGS. 16A-16B), mouse hippocampus (FIGS. 17A-17B), and mouse striatum (FIGS. 19A-19B).

---

What is claimed is:

1. A modified vector of an AAV-8 serotype, wherein the nucleotide sequence of the modified vector of the AAV-8 serotype is set forth in SEQ ID NO: 1.

2. An in vitro method for infecting a retinal ganglion cell, a Neuro2A cell, a U251 cell, a ARPE-19 cell, a SH-SY-5Y cell, a BV2 cell, a primary isolated HBMEC cell, a JURKAT cell, a K562 cell, or a THP1 cell comprising a step of adding the modified vector of claim 1 to a cell culture.

* * * * *

SEQUENCE LISTING

Sequence total quantity: 7
SEQ ID NO: 1            moltype = DNA  length = 7320
FEATURE                 Location/Qualifiers
source                  1..7320
                        mol_type = other DNA
                        organism = synthetic construct
SEQUENCE: 1
ccgccatgcc ggggtttac gagattgtga ttaaggtccc cagcgacctt gacgagcatc      60
tgcccggcat ttctgacagc tttgtgaact gggtggccga gaaggaatgg gagttgccgc     120
cagattctga catggatctg aatctgattg agcaggcacc cctgaccgtg gccgagaagc     180
tgcagcgcga ctttctgacg gaatggcgcc gtgtgagtaa ggccccggag gctcttttct     240
ttgtgcaatt tgagaaggga gagagctact tccacatgca cgtgctcgtg gaaaccaccg     300
gggtgaaatc catggttttg ggacgtttcc tgagtcagat tcgcgaaaaa ctgattcaga     360
gaatttaccg cgggatcgag ccgactttgc caaactggtt cgccggtcaca aagaccagaa    420
atggcgccgg aggcgggaac aaggtggtgg atgagtgcta catccccaat tacttgctcc     480
ccaaaaccca gcctgagctc cagtgggcgt ggactaatat ggaacagtat ttaagcgcct     540
gtttgaatct cacggagcgt aaacggttgg tggcgcagca tctgacgcac gtgtcgcaga     600
cgcaggagca gaacaaagag aatcagaatc ccaattctga tgcgccggtg atcagatcaa     660
aaacttcagc caggtacatg gagctggtcg ggtggctcgt ggacaagggg attacctcgg     720
agaagcagtg gatccaggag gaccaggcct catacatctc cttcaatgcg gcctccaact     780
cgcggtccca aatcaaggct gccttggaca atgcgggaa gattatgagc ctgactaaaa    840
ccgcccccga ctacctggtg ggccagcagc ccgtggagga catttccagc aatcggattt     900
ataaaatttt ggaactaaac gggtacgatc cccaatatgc ggcttccgtc tttctgggat     960
gggccacgaa aaagttcggc aagaggaaca ccatctggct gtttgggcct gcaactaccg    1020
ggaagaccaa catcgcggag gccatagccc acactgtgcc cttctacggg tgcgtaaact    1080
ggaccaatga gaactttccc ttcaacgact gtgtcgacaa gatggtgatc tggtgggagg    1140
aggggaagat gaccgccaag gtcgtggagt cggccaaagc cattctcgga ggaagcaagg    1200
tgcgcgtgga ccagaaatgc aagtcctcgg cccagataga cccgactccc gtgatcgtca    1260
cctccaacac caacatgtgc gccgtgattg acggggaactc aacgaccttc gaacaccagc    1320
agccgttgca agaccggatg ttcaaatttg aactcacccg ccgtctggat catgactttg    1380
ggaaggtcac caagcaggaa gtcaaagact ttttccggtg ggcaaaggat cacgtggttg     1440
aggtggagca tgaattctac gtcaaaaagg gtggagccaa gaaaagaccc gccccagtg    1500
acgcagatat aagtgagccc aaacgggtgc gcgagtcagt tgcgcagcca tcgacgtcag    1560
acgcggaagc ttcgatcaac tacgcagaca ggtaccaaaa caaatgttct cgtcacgtgg     1620
gcatgaatct gatgctgttt ccctgcagac aatgcgagag aatgaatcag aattcaaata    1680
tctgcttcac tcacggacag aaagactgtt tagagtgctt tcccgtgtca gaatctcaac    1740
ccgtttctgt cgtcaaaaag gcgtatcaga aactgtgcta cattcatcat atcatgggaa    1800
aggtgccaga cgcttgcact gcctgcgatc tggtcaatgt ggatttggat gactgcatct    1860
ttgaacaata aatgatttaa atcaggtatg gctgccgatg gttatcttcc agattggctc     1920
gaggacaacc tctctgaggg cattcgcgag tggtgggcgc tgaaacctgg agccccgaag    1980
cccaaagcca accagcaaaa gcaggacgac ggccggggtc tggtgcttcc tggctacaag     2040
tacctcggac ccttcaacgg actcgacaag ggggagcccg tcaacgcggc ggacgcagcg     2100
gccctcgagc acgacaaggc ctacgaccag cagctgcagg cgggtgacaa tccgtacctg     2160
cggtataacc acgccgacgc cgagtttcag gagcgtctgc aagaagatac gtcttttggg     2220
ggcaacctcg ggcgagcagt cttccaggcc aagaagcggg ttctcgaacc tctcggtctg     2280
gttgaggaag gcgctaagac ggctcctgga aagaagagac cggtagagcc atcaccccag     2340
cgttctccag actcctctac gggcatcggc aagaaaggcc aacagcccgc cagaaaaaga     2400
ctcaattttg gtcagactgg cgactcagag tcagttccag accctcaacc tctcggagaa     2460

-continued

```
cctccagcag cgccctctgg tgtgggacct aatacaatgg ctgcaggcgg tggcgcacca   2520
atggcagaca ataacgaagg cgccgacgga gtgggtagtt cctcgggaaa ttggcattgc   2580
gattccacat ggctgggcga cagagtcatc accaccagca cccgaacctg ggccctgccc   2640
acctacaaca accacctcta caagcaaatc tccaacggga catcgggagg agccaccaac   2700
gacaacacct acttcggcta cagcaccccc tgggggtatt ttgactttaa cagattccac   2760
tgccactttt caccacgtga ctggcagcga ctcatcaaca acaactgggg attccggccc   2820
aagagactca gcttcaagct cttcaacatc caggtcaagg aggtcacgca gaatgaaggc   2880
accaagacca tcgccaataa cctcaccagc accatccagg tgtttacgga ctcggagtac   2940
cagctgccgt acgttctcgg ctctgcccac cagggctgcc tgcctccgtt cccggcggac   3000
gtgttcatga ttccccagta cggctaccta acactcaaca acggtagtca ggccgtggga   3060
cgctcctcct tctactgcct ggaatacttt ccttcgcaga tgctgagaac cggcaacaac   3120
ttccagttta cttacacctt cgaggacgtg cctttccaca gcagctacgc ccacagccag   3180
agcttggacc ggctgatgaa tcctctgatt gaccagtacc tgtactactt gtctcggact   3240
caaacaacag gaggcacggc aaatacgcag actctgggct tcagccaagg tgggcctaat   3300
acaatggcca atcaggcaaa gaactggctg ccaggaccct gttaccgcca acaacgcgtc   3360
tcaacgacaa ccgggcaaaa caacaatagc aactttgcct ggactgctgg gaccaaatac   3420
catctgaatg gaagaaattc attggctaat cctggcatcg ctatggcaac acacaaagac   3480
gacgaggagc gtttttttcc cagtaacggg atcctgattt ttggcaaaca aaatgctgcc   3540
agagacaatg cggattacag cgatgtcatg ctcaccagca aggaagaaat caaaaccact   3600
aaccctgtgg ctacagagga atacggtatc gtggcagata acttgcagca gcaaaacttg   3660
gctagaggtg atagcacaaa gtctgccacg gctcctcaaa ttggaactgt caacagccag   3720
ggggccttac ccggtatggt ctggcagaac cgggacgtgt acctgcaggg tcccatctgg   3780
gccaagattc ctcacacggt cggcaacttc cacccctctc cgctgatggg cggctttggc   3840
ctgaaacatc ctccgcctca gatcctgatc aagaacacgc ctgtacctgc ggatcctccg   3900
accaccttca accagtcaaa gctgaactct ttcatcacgc aatacagcac cggacaggtc   3960
agcgtggaaa ttgaatggga gctgcagaag gaaaacgaca agcggtggga ccccgagatc   4020
cagtacacct ccaactacta caaatctaca agtgtggact ttgctgttaa tacagaaggc   4080
gtgtactctg aaccccgccc cattggcacc cgttacctca cccgtaatct gtaattgcct   4140
gttaatcaat aaaccggttg attcgtttca gttgaacttt ggtctctgcg aagggcgaat   4200
tcgtttaaac ctgcaggact agaggtcctg tattagaggt cacgtgagtg ttttgcgaca   4260
ttttgcgaca ccatgtggtc acgctgggta tttaagcccg agtgagcacg cagggtctcc   4320
attttgaagc gggaggtttg aacgcgcagc cgccaagccg aattctgcag atatccatca   4380
cactggcggc cgctcgacta gagcggccgc caccgcggtg gagctccagc ttttgttccc   4440
tttagtgagg gttaattgcg cgcttggcgt aatcatggtc atagctgttt cctgtgtgaa   4500
attgttatcc gctcacaatt ccacacaaca tacgagccgg aagcataaag tgtaaagcct   4560
ggggtgccta atgagtgagc taactcacat taattgcgtt gcgctcactg cccgctttcc   4620
agtcgggaaa cctgtcgtgc cagctgcatt aatgaatcgg ccaacgcgcg gggagaggcg   4680
gtttgcgtat tgggcgctct tccgcttcct cgctcactga ctcgctgcgc tcggtcgttc   4740
ggctgcggcg agcggtatca gctcactcaa aggcggtaat acggttatcc acagaatcag   4800
gggataacgc aggaaagaac atgtgagcaa aaggccagca aaaggccagg aaccgtaaaa   4860
aggccgcgtt gctggcgttt ttccataggc tccgcccccc tgacgagcat cacaaaaatc   4920
gacgctcaag tcagaggtgg cgaaacccga caggactata aagataccag gcgtttcccc   4980
ctggaagctc cctcgtgcgc tctcctgttc cgaccctgcc gcttaccgga tacctgtccg   5040
cctttctccc ttcgggaagc gtggcgcttt ctcatagctc acgctgtagg tatctcagtt   5100
cggtgtaggt cgttcgctcc aagctgggct gtgtgcacga accccccgtt cagcccgacc   5160
gctgcgcctt atccggtaac tatcgtcttg agtccaaccc ggtaagacac gacttatcgc   5220
cactggcagc agccactggt aacaggatta gcagagcgag gtatgtaggc ggtgctacag   5280
agttcttgaa gtggtggcct aactacggct acactagaag aacagtattt ggtatctgcg   5340
ctctgctgaa gccagttacc ttcggaaaaa gagttggtag ctcttgatcc ggcaaacaaa   5400
ccaccgctgg tagcggtggt ttttttgttt gcaagcagca gattacgcgc agaaaaaaag   5460
gatctcaaga agatcctttg atcttttcta cggggtctga cgctcagtgg aacgaaaact   5520
cacgttaagg gattttggtc atgagattat caaaaaggat cttcacctag atccttttaa   5580
attaaaaatg aagttttaaa tcaatctaaa gtatatatga gtaaacttgg tctgacagtt   5640
accaatgctt aatcagtgag gcacctatct cagcgatctg tctatttcgt tcatccatag   5700
ttgcctgact ccccgtcgtg tagataacta cgatacggga gggcttacca tctggcccca   5760
gtgctgcaat gataccgcga gacccacgct caccggctcc agatttatca gcaataaacc   5820
agccagccgg aagggccgag cgcagaagtg gtcctgcaac tttatccgcc tccatccagt   5880
ctattaattg ttgccgggaa gctagagtaa gtagttcgcc agttaatagt ttgcgcaacg   5940
ttgttgccat tgctacaggc atcgtggtgt cacgctcgtc gtttggtatg gcttcattca   6000
gctccggttc ccaacgatca aggcgagtta catgatcccc catgttgtgc aaaaaagcgg   6060
ttagctcctt cggtcctccg atcgttgtca gaagtaagtt ggccgcagtg ttatcactca   6120
tggttatggc agcactgcat aattctctta ctgtcatgcc atccgtaaga tgcttttctg   6180
tgactggtga gtactcaacc aagtcattct gagaatagtg tatgcggcga ccgagttgct   6240
cttgcccggc gtcaatacgg gataataccg cgccacatag cagaacttta aaagtgctca   6300
tcattggaaa acgttcttcg gggcgaaaac tctcaaggat cttaccgctg ttgagatcca   6360
gttcgatgta acccactcgt gcacccaact gatcttcagc atcttttact ttcaccagcg   6420
tttctgggtg agcaaaaaca ggaaggcaaa atgccgcaaa aaagggaata agggcgacac   6480
ggaaatgttg aatactcata ctcttccttt ttcaatatta ttgaagcatt tatcagggtt   6540
attgtctcat gagcggatac atatttgaat gtatttagaa aaataaacaa ataggggttc   6600
cgcgcacatt tccccgaaaa gtgccaccta aattgtaagc gttaatattt tgttaaaatt   6660
cgcgttaaat ttttgttaaa tcagctcatt ttttaaccaa taggccgaaa tcggcaaaat   6720
cccttataaa tcaaaagaat agaccgagat agggttgagt gttgttccag tttggaacaa   6780
gagtccacta ttaaagaacg tggactccaa cgtcaaaggg cgaaaaaccg tctatcaggg   6840
cgatggccca ctacgtgaac catcacccta atcaagtttt ttggggtcga ggtgccgtaa   6900
agcactaaat cggaacccta aagggagccc ccgatttaga gcttgacggg gaaagccggc   6960
gaacgtggcg agaaaggaag ggaagaaagc gaaaggagcg ggcgctaggg cgctggcaag   7020
tgtagcggtc acgctgcgcg taaccaccac acccgccgcg cttaatgcgc cgctacaggg   7080
cgcgtcccat tcgccattca ggctgcgcaa ctgttgggaa gggcgatcgg tgcgggcctc   7140
ttcgctatta cgccagctgg cgaaaggggg atgtgctgca aggcgattaa gttgggtaac   7200
```

```
gccagggttt tcccagtcac gacgttgtaa aacgacggcc agtgagcgcg cgtaatacga   7260
ctcactatag ggcgaattgg gtaccgggcc cccctcgat  cgaggtcgac ggtatcgggg   7320

SEQ ID NO: 2              moltype = DNA  length = 7336
FEATURE                   Location/Qualifiers
source                    1..7336
                          mol_type = other DNA
                          organism = synthetic construct
SEQUENCE: 2
ccgccatgcc ggggtttttac gagattgtga ttaaggtccc cagcgcacctt gacgagcatc   60
tgcccggcat ttctgacagc tttgtgaact gggtggccga gaaggaatgg gagttgccgc  120
cagattctga catggatctg aatctgattg agcaggcacc cctgaccgtg gccgagaagc  180
tgcagcgcga ctttctgacg gaatggcgcc gtgtgagtaa ggccccggag gctctttttct  240
ttgtgcaatt tgagaaggga gagagctact tccacatgca cgtgctcgtg gaaaccaccg  300
gggtgaaatc catggttttg ggacgtttcc tgagtcagat tcgcgaaaaa ctgattcaga  360
gaatttaccg cgggatcgag ccgactttgc caaactggtt cgcggtcaca aagaccagaa  420
atggcgccgg aggcgggaac aaggtggtgg atgagtgcta catccccaat tacttgctcc  480
ccaaaaccca gcctgagctc cagtgggcgt ggactaatat ggaacagtat ttaagcgcct  540
gtttgaatct cacggagcgt aaacggttgg tggcgcagca tctgacgcac gtgtcgcaga  600
cgcaggagca gaacaaagag aatcagaatc ccaattctga tgcgccggtg atcagatcaa  660
aaacttcagc caggtacatg gagctggtcg ggtggctcgt ggacaagggg attacctcgg  720
agaagcagtg gatccaggag gaccaggcct catacatctc cttcaatgcg gcctccaact  780
cgcggtccca aatcaaggct gccttggaca atgcgggaaa gattatgagc ctgactaaaa  840
ccgcccccga ctacctggtg ggccagcagc ccgtggagga catttccagc aatcggattt  900
ataaaatttt ggaactaaac gggtacgatc cccaatatgc ggcttccgtc tttctgggat  960
gggccacgaa aaagttcggc aagaggaaca ccatctgcgt gtttgggcct gcaactaccg  1020
ggaagaccaa catcgcggag gccatagccc acactgtgcc cttctacggg tgcgtaaact  1080
ggaccaatga gaactttccc ttcaacgact gtgtcgacaa gatggtgatc tggtgggagg  1140
aggggaagat gaccgccaag gtcgtggagt cggccaaagc cattctcgga ggaagcaagg  1200
tgcgcgtgga ccagaaatgc aagtcctcgg cccagataga cccgactccc gtgatcgtca  1260
cctccaacac caacatgtgc gccgtgattg acgggaactc aacgaccttc gaacaccagc  1320
agccgttgca agaccggatg ttcaaatttg aactcacccg ccgtctggat catgactttg  1380
ggaaggtcac caagcaggaa gtcaaagact ttttccggtg ggcaaaggat cacgtggttg  1440
aggtggagca tgaattctac gtcaaaaagg gtggagccaa gaaaagaccc gcccccagtg  1500
acgcagatat aagtgagccc aaacgggtgc gcgagtcagt tgcgcagcca tcgacgtcaa  1560
acgcggaagc ttcgatcaac tacgcagaca ggtaccaaaa caaatgttct cgtcacgtgg  1620
gcatgaatct gatgctgttt ccctgcgac  aatgcgagag aatgaatcag aattcaaata  1680
tctgcttcac tcacggacag aaagactgtt tagagtgctt tcccgtgtca gaatctcaac  1740
ccgtttctgt cgtcaaaaag gcgtatcaga aactgtgcta cattcatcat atcatgggaa  1800
aggtgccaga cgcttgcact gcctgcgatc tggtcaatgt ggatttggat gactgcatct  1860
ttgaacaata aatgatttaa atcaggtatg gctgccgatg gttatcttcc agattggctc  1920
gaggacaacc tctctgaggg cattcgcgag tggtgggcgc tgaaacctgg agccccgaag  1980
cccaaagcca accagcaaaa gcaggacgac ggccggggtc tggtgcttcc tggctacaag  2040
tacctcggac ccttcaacgg actcgacaag ggggagcccg tcaacgcggc ggacgcagcg  2100
gccctcgagc acgacaaggc ctacgaccag cagctgcagg cgggtgacaa tccgtacctg  2160
cggtataacc acgccgacgc cgagtttcag gagcgtctgc aagaagatac gtcttttggg  2220
ggcaacctcg ggcgagcagt cttccaggcc aagaagcggt ttctcgaacc tctcggtctg  2280
gttgaggaag cgcgctaagac ggctcctgga aagaagagac cggtagagcc atcaccccag  2340
cgttctccag actcctctac gggcatcggc aagaaaggcc aacagcccgc cagaaaaaga  2400
ctcaattttg gtcagactgg cgactcagag tcagttccag accctcaacc tctcggagaa  2460
cctccagcag cgccctctgg tgtgggacct aatacaatgg ctgcaggcgg tggcgcacca  2520
atggcagaca ataacgaagg cgccgacgga gtgggtagtt cctcgggaaa ttggcattgc  2580
gattccacat ggctgggcga cagagtcatc accaccagca cccgaacctg ggccctgccc  2640
acctacaaca accacctcta caagcaaatc tccaacggga catcgggagg agccaccaac  2700
gacaacacct acttcggcta cagcaccccc tgggggtact ttgactttaa cagattccac  2760
tgccactttt caccacgtga ctggcagcga ctcatcaaca caaactgggg attccggccc  2820
aagagactca gcttcaagct cttcaacatc caggtcaagg aggtcacgca gaatgaaggc  2880
accaagacca tcgccaataa cctcaccagc accatccagg tgtttacgga ctcggagtac  2940
cagctgccgt acgttctcgg ctctgccac  cagggctgcc tgcctccgtt cccgagcggac  3000
gtgttcatga ttccccagta cggctacctta acactcaaca acggagtagtca acggcgtgga  3060
cgctcctcct tctactgcct ggaatacttt ccttcgcaga tgctgagaac cggcaacaac  3120
ttccagtttta cttacacctt cgaggacgtg cctttccaca gcagctacgc ccacagccag  3180
agcttggacc ggctgatgaa tcctctgatt gaccagtacc tgtactactt gtctcggact  3240
caaacaacag gaggcacggc aaatacgcag actctgggct tcagccaagg tgggcctaat  3300
acaatggcca tcaggcaaa  gaactggctg ccaggaccct gttaccgcca caacgcgtc   3360
tcaacgacaa ccgggcaaaa caacaatagc aacttgcct  ggactgctgg gaccaaatac  3420
catctgaatg gaagaaattc attggctaat cctggcatcg ctatggcaac acacaaagac  3480
gacgaggagc gtttttttcc cagtaacggg atcctgattt ttggcaaaca aaatgctgcc  3540
agagacaatg cggattacag cgatgtcatg ctcaccaggg aggaagaaat caaaaccaat  3600
aaccctgtgg ctacagagga atacggtatc gtgtgcagata acttgcagca gcaaaacacg  3660
gctcctcaaa ttggaactgt caacagccag ggggccttac ccgtatggt  ctggcagaac  3720
cgggacgtgt acctgcaggg tcccatctgg gccaagattc tcacacggga cggcaacttc  3780
cacccgtctc cgctgatggg cggctttggc ctgaaacatc ctccgcctca gatcctgatc  3840
aagaacacct acttcggcta ggatcctccg accaccttca accagtcaaa gctgaactct  3900
ttcatcacgc aatacagcac cggacaggtc agcgtggaaa ttgaatggga gctgcagaag  3960
gaaaacagca gcgctggaa  ccccgagatc cagtacacct ccaactacta caaatctaca  4020
agtgtggact ttgctgttaa tacagaaggc gtgtactctg aaccccgccc cattggcacc  4080
cgttacctca cccgtaatct gtaattgcct gttaatcaat aaaccggttg attcgtttca  4140
gttgaacttt ggtctctgcg aagggcgaat tcgtttaaac ctgcaggact agaggtcctg  4200
```

-continued

```
tattagaggt cacgtgagtg ttttgcgaca ttttgcgaca ccatgtggtc acgctgggta   4260
tttaagcccg agtgagcacg cagggtctcc attttgaagc gggaggtttg aacgcgcagc   4320
cgccaagccg aattctgcag atatccatca cactggcggc cgctcgacta gagcggccgc   4380
caccgcggtg gagctccagc tttttgttccc tttagtgagg gttaattgcg cgcttggcgt   4440
aatcatggtc atagctgttt cctgtgtgaa attgttatcc gctcacaatt ccacacaaca   4500
tacgagccgg aagcataaag tgtaaagcct ggggtgccta atgagtgagc taactcacat   4560
taattgcgtt gcgctcactg cccgctttcc agtcgggaaa cctgtcgtgc cagctgcatt   4620
aatgaatcgg ccaacgcgcg gggagaggcg gtttgcgtat tgggcgctct ccgcttcct   4680
cgctcactga ctcgctgcgc tcggtcgttc ggctgcggcg agcggtatca gctcactcaa   4740
aggcggtaat acggttatcc acagaatcag gggataacgc aggaaagaac atgtgagcaa   4800
aaggccagca aaaggccagg aaccgtaaaa aggccgcgtt gctggcgttt ttccataggc   4860
tccgcccccc tgacgagcat cacaaaaatc gacgctcaag tcagaggtgg cgaaacccga   4920
caggactata aagataccag gcgtttcccc ctggaagctc cctcgtgcgc tctcctgttc   4980
cgaccctgcc gcttaccgga tacctgtccg cctttctccc ttcgggaagc gtggcgcttt   5040
ctcatagctc acgctgtagg tatctcagtt cggtgtaggt cgttcgctcc aagctgggct   5100
gtgtgcacga accccccgtt cagcccgacc gctgcgcctt atccggtaac tatcgtcttg   5160
agtccaaccc ggtaagacac gacttatcgc cactggcagc agccactggt aacaggatta   5220
gcagagcgag gtatgtaggc ggtgctacag agttcttgaa gtggtggcct aactacggct   5280
acactagaag aacagtattt ggtatctgcg ctctgctgaa gccagttacc ttcggaaaaa   5340
gagttggtag ctcttgatcc ggcaaacaaa ccaccgctgg tagcggtggt ttttttgttt   5400
gcaagcagca gattacgcgc agaaaaaaag gatctcaaga agatcctttg atcttttcta   5460
cggggtctga cgctcagtgg aacgaaaact cacgttaagg gattttggtc atgagattat   5520
caaaaaggat cttcacctag atcctttaa attaaaaatg aagttttaaa tcaatctaaa   5580
gtatatatga gtaaacttgg tctgacagtt accaatgctt aatcagtgag gcacctatct   5640
cagcgatctg tctatttcgt tcatccatag ttgcctgact ccccgtcgtg tagataacta   5700
cgatacggga gggcttacca tctggcccca gtgctgcaat gataccgcga gacccacgct   5760
caccggctcc agatttatca gcaataaacc agccagccgg aagggccgag cgcagaagtg   5820
gtcctgcaac tttatccgcc tccatccagt ctattaattg ttgccgggaa gctagagtaa   5880
gtagttcgcc agttaatagt ttgcgcaacg ttgttgccat tgctacaggc atcgtggtgt   5940
cacgctcgtc gtttggtatg gcttcattca gctccggttc ccaacgatca aggcgagtta   6000
catgatcccc catgttgtgc aaaaaagcgg ttagctcctt cggtcctccg atcgttgtca   6060
gaagtaagtt ggccgcagtg ttatcactca tggttatggc agcactgcat aattctctta   6120
ctgtcatgcc atccgtaaga tgcttttctg tgactggtga gtactcaacc aagtcattct   6180
gagaatagtg tatgcggcga ccgagttgct cttgcccggc gtcaatacgg gataataccg   6240
cgccacatag cagaacttta aaagtgctca tcattggaaa acgttcttcg gggcgaaaac   6300
tctcaaggat cttaccgctg ttgagatcca gttcgatgta acccactcgt gcacccaact   6360
gatcttcagc atcttttact ttcaccagcg tttctgggtg agcaaaaaca ggaaggcaaa   6420
atgccgcaaa aaagggaata aggcgcacac ggaaatgttg aatactcata ctcttccttt   6480
ttcaatatta ttgaagcatt tatcagggtt attgtctcat gagcggatac atatttgaat   6540
gtatttagaa aaataaacaa ataggggttc cgcgcacatt tccccgaaaa gtgccaccta   6600
aattgtaagc gttaatattt tgttaaaatt cgcgttaaat ttttgttaaa tcagctcatt   6660
ttttaaccaa taggccgaaa tcggcaaaat cccttataaa tcaaaagaat agaccgagat   6720
agggttgagt gttgttccag tttggaacaa gagtccacta ttaaagaacg tggactccaa   6780
cgtcaaaggg cgaaaaaccg tctatcaggg cgatggccca ctacgtgaac catcacccta   6840
atcaagtttt ttggggtcga ggtgccgtaa agcactaaat cggaaccccta aagggagccc   6900
ccgatttaga gcttgacggg gaaagccggc gaacgtggcg agaaaggaag ggaagaaagc   6960
gaaaggagcg ggcgctaggg cgctggcaag tgtagcggtc acgctgcgcg taaccaccac   7020
acccgccgcg cttaatgcgc cgctacaggg cgcgtcccat tcgccattca ggctgcgcaa   7080
ctgttgggaa gggcgatcgg tgcgggcctc ttcgctatta cgccagctgg cgaaaggggg   7140
atgtgctgca aggcgattaa gttgggtaac gccaggggttt cccagtcac gacgttgtaa   7200
aacgacggcc agtgagcgcg cgtaatacga ctcactatag ggcgaattgg gtaccgggcc   7260
cccctcgat cgaggtcgac ggtatcgggg gagctcgcag ggtctccatt ttgaagcggg   7320
aggtttgaac gcgcag                                                   7336

SEQ ID NO: 3            moltype = AA   length = 10
FEATURE                 Location/Qualifiers
source                  1..10
                        mol_type = protein
                        organism = synthetic construct
SEQUENCE: 3
LARGDSTKSA                                                             10

SEQ ID NO: 4            moltype = DNA   length = 30
FEATURE                 Location/Qualifiers
source                  1..30
                        mol_type = other DNA
                        organism = synthetic construct
SEQUENCE: 4
ttggctagag gtgatagcac aaagtctgcc                                       30

SEQ ID NO: 5            moltype = DNA   length = 20
FEATURE                 Location/Qualifiers
source                  1..20
                        mol_type = other DNA
                        organism = synthetic construct
misc_feature            1..20
SEQUENCE: 5
aggaccctgt taccgccaac                                                  20
```

23                                                                                      24

-continued

```
SEQ ID NO: 6            moltype = DNA   length = 20
FEATURE                 Location/Qualifiers
source                  1..20
                        mol_type = other DNA
                        organism = synthetic construct
misc_feature            1..20
SEQUENCE: 6
gatgtttcag gccaaagccg                                           20

SEQ ID NO: 7            moltype = DNA   length = 87
FEATURE                 Location/Qualifiers
source                  1..87
                        mol_type = other DNA
                        organism = synthetic construct
SEQUENCE: 7
gtggcagata acttgcagca gcaaaacttg gctagaggtg atagcacaaa gtctgccacg  60
gctcctcaaa ttggaactgt caacagc                                    87
```